United States Patent
Freeman et al.

(10) Patent No.: US 9,592,401 B2
(45) Date of Patent: Mar. 14, 2017

(54) AUTOMATED PEDIATRIC DEFIBRILLATOR

(71) Applicant: ZOLL Medical Corporation, Chelmsford, MA (US)

(72) Inventors: Gary A. Freeman, Newton Center, MA (US); Ziad F. Elghazzawi, Newton, MA (US); Frederick J. Geheb, Danvers, MA (US); Michael Parascandola, Londonderry, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/269,572

(22) Filed: May 5, 2014

(65) Prior Publication Data
US 2014/0243915 A1 Aug. 28, 2014

Related U.S. Application Data

(62) Division of application No. 11/104,272, filed on Apr. 12, 2005, now Pat. No. 8,738,130.
(Continued)

(51) Int. Cl.
*A61N 1/39* (2006.01)
*A61N 1/04* (2006.01)
*A61B 5/00* (2006.01)

(52) U.S. Cl.
CPC .......... *A61N 1/3918* (2013.01); *A61B 5/4836* (2013.01); *A61N 1/046* (2013.01);
(Continued)

(58) Field of Classification Search
CPC ........ A61N 1/046; A61N 1/0492; A61N 1/39; A61N 1/3925; A61N 1/3918;
(Continued)

(56) References Cited

U.S. PATENT DOCUMENTS

| 5,496,257 A | 3/1996 | Kelly |
| 5,666,104 A * | 9/1997 | Pollack ................. A61B 5/107 340/573.1 |

(Continued)

FOREIGN PATENT DOCUMENTS

WO 02/091905 11/2002

OTHER PUBLICATIONS

AHA Guidelines 2000 for Cardiopulmonary Resuscitation and Emergency Cardiovascular Care, Supplement to Circulation, vol. 102, No. 8, Part 3: Adult Basic Life Support, p. 1-32, Figs. 7 and 8 (Aug. 22, 2000).

(Continued)

*Primary Examiner* — Catherine Voorhees
(74) *Attorney, Agent, or Firm* — Fish & Richardson P.C.

(57) ABSTRACT

A device for assisting a rescuer in delivering therapy to an adult or pediatric patient, the device including a user interface comprising a display and/or audio speakers, the user interface being configured to deliver prompts to a rescuer to assist the rescuer in delivering therapy to a patient; a processor configured to provide prompts to the user interface and to perform an ECG analysis algorithm on ECG information detected from the patient; at least one detection element configured to determine without rescuer input via the user interface that a pediatric patient is being treated; wherein, if a pediatric patient is detected, the processor modifies the ECG analysis algorithm or the prompts provided to the user interface to use an ECG analysis algorithm or prompts adapted for a pediatric patient rather than for an adult patient.

17 Claims, 17 Drawing Sheets

Related U.S. Application Data

(60) Provisional application No. 60/561,493, filed on Apr. 12, 2004.

(52) U.S. Cl.
CPC ............. *A61N 1/0492* (2013.01); *A61N 1/39* (2013.01); *A61N 1/3906* (2013.01); *A61N 1/3925* (2013.01); *A61N 1/3968* (2013.01); *A61N 1/3993* (2013.01)

(58) Field of Classification Search
CPC .. A61N 1/3993; A61N 1/3906; A61N 1/3968; A61B 5/4836
See application file for complete search history.

(56) References Cited

U.S. PATENT DOCUMENTS

| | | | |
|---|---|---|---|
| 6,065,154 | A | 5/2000 | Hulings et al. |
| 6,101,413 | A | 8/2000 | Olson et al. |
| 6,125,299 | A | 9/2000 | Groenke et al. |
| 6,134,468 | A | 10/2000 | Morgan et al. |
| 6,351,671 | B1 | 2/2002 | Myklebust et al. |
| 6,356,785 | B1 | 3/2002 | Snyder et al. |
| 2002/0177793 | A1 | 11/2002 | Sherman et al. |
| 2003/0040775 | A1 | 2/2003 | Faller et al. |
| 2003/0055478 | A1 | 3/2003 | Lyster et al. |
| 2003/0195567 | A1* | 10/2003 | Jayne ................ A61N 1/39 607/5 |
| 2004/0082888 | A1 | 4/2004 | Palazzolo et al. |
| 2004/0116969 | A1* | 6/2004 | Owen ................ A61B 5/02416 607/6 |
| 2004/0162586 | A1* | 8/2004 | Covey ................ A61N 1/0472 607/5 |
| 2004/0267324 | A1 | 12/2004 | Geheb et al. |

OTHER PUBLICATIONS

AHA Guidelines 2000 for Cardiopulmonary Resuscitation and Emergency Cardiovascular Care, Supplement to Circulation, vol. 102, No. 8, Part 4: Automated External Defibrillator, p. 1-67 (Aug. 22, 2000).

Atkinson et al., "Specificity and Sensitivity of Automated External Defibrillator Rhythm Analysis in Infants and Children," Annals of Emergency Medicine 42(2):185-186 (Aug. 2003).

Cecchin et al., "Is Arrhythmia Detection by Automatic External Defibrillator Accurate for Children?" Circulation 103:2483-2488 (May 2001).

Garson, Table of Contents and Index for the Electrocardiogram in Infants and Children, Published by Lea & Febiger, Philadelphia, PA (1983).

Kerber et al., "Automatic External Defibrillators for Public Access Defibrillation: Recommendations for Specifying and Reporting Arrhythmia Analysis Algorithm Performance, Incorporating New Waveforms, and Enhancing Safety," Circulation 95(6):1677-1682 (Mar. 1987).

Tacker, Defibrillation of the Heart ICDs, AEDs, and Manual, Chapter 12: Cardiac Damage from Transchest and ICD Defibrillator Shocks by Van Vleet et al. (1994).

\* cited by examiner

| Rhythm | Mean Peak-Peak Signal Amplitude | Iso-electric Measure | Mean Heart Rate | Rate Variance | Mean Width | Advisory Decision |
|---|---|---|---|---|---|---|
| VF | > MINIMUM AMP LIMIT | < ADULT VF ISO LIMIT | | | | SHOCKABLE |
| VT | > MINIMUM AMP LIMIT | < ADULT VT ISO LIMIT | ≥ ADULT VT RATE LIMIT | | ≥ ADULT ABNORMAL LIMIT | SHOCKABLE |
| NSR | > MINIMUM AMP LIMIT | ≥ ADULT NSR ISO LIMIT | < ADULT NSR RATE LIMIT | < ADULT NSR VARIANCE LIMIT | < ADULT ABNORMAL LIMIT | NON-SHOCKABLE |
| ABNORMAL | > MINIMUM AMP LIMIT | ≥ ADULT ABN ISO LIMIT | < ADULT ABN RATE LIMIT | ≥ ADULT NSR VARIANCE LIMIT | | NON-SHOCKABLE |
| ASYSTOLE | ≤ 100 uv | NA | NA | NA | NA | NON-SHOCKABLE |
| FINE VF | > MINIMUM AMP LIMIT & < MAX FVF AMP LIMIT | < ADULT FVF ISO LIMIT | | | | SHOCKABLE |
| OTHER VT | > MINIMUM AMP LIMIT | < ADULT OVT ISO LIMIT | < ADULT VT RATE LIMIT | | ≥ ADULT ABNORMAL LIMIT | NON-SHOCKABLE |

FIG. 15

| Rhythm | Mean Peak-Peak Signal Amplitude | Iso-electric Measure | Mean Heart Rate | Rate Variance | Mean Width | Advisory Decision |
|---|---|---|---|---|---|---|
| VF | > MINIMUM AMP LIMIT | < PEDI VF ISO LIMIT | | | | SHOCKABLE |
| VT | > MINIMUM AMP LIMIT | < PEDI VT ISO LIMIT | ≥ PEDI VT RATE LIMIT | | ≥ PEDI ABNORMAL LIMIT | SHOCKABLE |
| NSR | > MINIMUM AMP LIMIT | ≥ PEDI NSR ISO LIMIT | < PEDI NSR RATE LIMIT | < PEDI NSR VARIANCE LIMIT | < PEDI ABNORMAL LIMIT | NON-SHOCKABLE |
| ABNORMAL | > MINIMUM AMP LIMIT | ≥ PEDI ABN ISO LIMIT | < PEDI ABN RATE LIMIT | ≥ PEDI NSR VARIANCE LIMIT | | NON-SHOCKABLE |
| ASYSTOLE | ≤ 100 uv | NA | NA | NA | NA | NON-SHOCKABLE |
| FINE VF | > MINIMUM AMP LIMIT & < MAX FVF AMP LIMIT | < PEDI FVF ISO LIMIT | | | | SHOCKABLE |
| OTHER VT | > MINIMUM AMP LIMIT | < PEDI OVT ISO LIMIT | < PEDI VT RATE LIMIT | | ≥ PEDI ABNORMAL LIMIT | NON-SHOCKABLE |

FIG. 16

AUTOMATED PEDIATRIC DEFIBRILLATOR

CROSS-REFERENCE TO RELATED APPLICATIONS

This application is a divisional application of and claims priority to U.S. application Ser. No. 11/104,272, filed on Apr. 12, 2005, which application claims priority to U.S. Provisional Application No. 60/561,493, filed on Apr. 12, 2004. Both applications are hereby incorporated by reference.

TECHNICAL FIELD

This invention relates to the treatment of cardiac arrest in pediatric populations with automatic external defibrillators (AEDs).

BACKGROUND

Automatic External Defibrillators (AEDs) are used by non-medical personnel to defibrillate victims of cardiac arrest the prevalence of which is approximately 600,000 people per year, worldwide. In the past, these AEDs had only been available for the adult population, and the pediatric arrest victims were forced to wait valuable minutes for the professional rescuers such as paramedics, doctors or nurses to arrive. AEDs are now available that are designed specifically to be compatible for use on children. Because defibrillation energies are lower with children, various methods have been developed to accommodate this fact and provide a means of switching defibrillation energies if a pediatric arrest victim is present. One method, described in U.S. Pat. No. 6,101,413, determines a pediatric arrest victim is present if the AED detects that electrodes specifically designed for use with children are attached to the device, in which case the energy levels and voice prompts associated with energy delivery are adjusted to conform with those most appropriate for children. U.S. Patent Application 2003/0195567A1 describes a method that determines a victim is a child based on user input form the AED operator. The energy levels are set based on such indirect means as a measurement of the patient, e.g., the length of an anatomical feature of the victim may be correlated within the AED to a specific energy level.

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. The term basic life support (BLS) involves all the following elements: initial assessment; airway maintenance; expired air ventilation (rescue breathing); and chest compression. When all three [airway breathing, and circulation, including chest compressions] are combined, the term cardiopulmonary resuscitation (CPR) is used. In the case of pediatric arrest, CPR takes on a heightened prominence based on the fact that cardiac arrest is rare in children, and many more children are affected by respiratory arrest due to choking, drowning, poisoning and asthma.

There are many different kinds of abnormal heart rhythms, some of which can be treated by defibrillation therapy ("shockable rhythms") and some which cannot (non-shockable rhythms"). For example, most ECG rhythms that produce significant cardiac output are considered non-shockable (examples include normal sinus rhythms, certain bradycardias, and sinus tachycardias). There are also several abnormal ECG rhythms that do not result in significant cardiac output but are still considered non-shockable, since defibrillation treatment is usually ineffective under these conditions. Examples of these non-shockable rhythms include asystole, electromechanical disassociation and other pulseless electrical activity. Although a patient cannot remain alive with these non-viable, non-shockable rhythms, applying shocks will not help convert the rhythm. The primary examples of shockable rhythms, for which the caregiver should perform defibrillation, include ventricular fibrillation, ventricular tachycardia, and ventricular flutter.

The current protocols recommended by the American Heart Association (AHA) are as follows: after using a defibrillator to apply one or more shocks to a patient who has a shockable ECG rhythm, the patient may nevertheless remain unconscious, in a shockable or non-shockable, perfusing or non-perfusing rhythm. If a non-perfusing rhythm is present, the caregiver may then resort to performing CPR for a period of time in order to provide continuing blood flow and oxygen to the patient's heart, brain and other vital organs. If a shockable rhythm continues to exist or develops during the delivery of CPR, further defibrillation attempts may be undertaken following this period of cardiopulmonary resuscitation. As long as the patient remains unconscious and without effective circulation, the caregiver can alternate between use of the defibrillator (for analyzing the electrical rhythm and possibly applying a shock) and performing cardio-pulmonary resuscitation (CPR). CPR generally involves a repeating pattern of five or fifteen chest compressions followed by a pause during which two rescue breaths are given.

Defibrillation can be performed using an AED. The American Heart Association, European Resuscitation Council, and other similar agencies provide protocols for the treatment of victims of cardiac arrest that include the use of AEDs. These protocols define a sequence of steps to be followed in accessing the victim's condition and determining the appropriate treatments to be delivered during resuscitation. Caregivers who may be required to use an AED are trained to follow these protocols.

Most automatic external defibrillators are actually semi-automatic external defibrillators (SAEDs), which require the caregiver to press a start or analyze button, after which the defibrillator analyzes the patient's ECG rhythm and advises the caregiver to provide a shock to the patient if the electrical rhythm is shockable. The caregiver is then responsible for pressing a control button to deliver the shock. Following shock delivery, the SAED may reanalyze the patient's ECG rhythm, automatically or manually, and advise additional shocks or instruct the caregiver to check the patient for signs of circulation (indicating that the defibrillation treatment was successful or that the rhythm is non-shockable) and to begin CPR if circulation has not been restored by the defibrillation attempts. Fully automatic external defibrillators, on the other hand, do not wait for user intervention before applying defibrillation shocks. As used below, automatic external defibrillators (AEDs) include semi-automatic external defibrillators (SAEDs).

Automated External Defibrillators include signal processing software that analyzes ECG signals acquired from the victim to determine when a cardiac arrhythmia such as Ventricular Fibrillation (VF) or shockable ventricular tachycardia (VT) exists. Usually, these algorithms are designed to perform ECG analyses at specific times during the rescue event. The first ECG analysis is usually initiated within a few seconds following attachment of the defibrillation electrodes to the patient. Subsequent ECG analyses may or may not be initiated based upon the results of the first analysis. Typically if the first analysis detects a shockable rhythm, the rescuer is advised to deliver a defibrillation shock. Following the shock delivery a second analysis is automatically initiated to determine whether the defibrillation treatment was successful or not (i.e. the shockable ECG rhythm has been converted to a normal or other non-shockable rhythm). If this second analysis detects the continuing presence of a shockable arrhythmia, the AED advises the user to deliver a second defibrillation treatment. A third ECG analysis may then be initiated to determine whether the second shock was or was not effective. If a shockable rhythm persists, the rescuer is then advised to deliver a third defibrillation treatment.

The typical algorithms process the ECG for measured features which will differentiate the rhythm as shockable (ventricular fibrillation (VF) and ventricular tachycardia (VT)) or non-shockable rhythms (normal sinus rhythms (NSR), abnormal rhythms (ABN), non-shockable VT's and asystole). Some of these features include R to R interval averaging, R to R interval variance, average and maximum signal amplitude, measures of baseline isoelectric time, QRS width, ECG first difference distributions, and parameters from frequency domain analysis' Analyses of annotated ECG databases establish the distribution of values for a given feature for shockable and non-shockable rhythms. Appropriate decision logic techniques can be used to combine this knowledge and produce the shock or non-shock decision.

Although AEDs have been designed for use on adults and the ECG arrhythmia logic has been developed for the adult population, there is a clear need to extend the use of AEDs to children with cardiac arrest. Recent literature have reported the accuracies of adult based AED arrhythmia algorithms on ECG databases collected from children and have concluded they are safe and effective. However, there are significant differences between adult and pediatric ECG rhythms. For example, the pediatric ECG exhibits faster normal heart rates, narrower QRS widths, and shorter PR and QT intervals as compared to adults. Shockable ventricular tachycardia occurs at much higher rates (>200 BPM) in pediatric subjects than adults (>150 BPM).

Following the third defibrillator shock or when any of the analyses described above detects a non-shockable rhythm, treatment protocols recommended by the American Heart Association and European Resuscitation Council require the rescuer to check the patient's pulse or to evaluate the patient for signs of circulation. If no pulse or signs of circulation are present, the rescuer is trained to perform CPR on the victim for a period of one or more minutes. Following this period of cardiopulmonary resuscitation (that includes rescue breathing and chest compressions) the AED reinitiates a series of up to three additional ECG analyses interspersed with appropriate defibrillation treatments as described above. The sequence of 3 ECG analyses/defibrillation shocks followed by 1-3 minutes of CPR, continues in a repetitive fashion for as long as the AED's power is turned on and the patient is connected to the AED device. Typically, the AED provides audio prompts to inform the rescuer when analyses are about to begin, what the analysis results were and when to start and stop the delivery of CPR.

The AED can be used on adult and pediatric patients. However, the American Heart Association recommends a different protocol in the rescue of pediatric victims compared to the adult rescue protocol particularly with regards to the application of CPR. Because of the heightened prominence of airway and breathing with pediatric arrest victims, the AHA recommends that prior even to calling and activating emergency medical services (EMS) system, the child's airway is first checked for obstructions, the airway is cleared, and mouth to mouth breathing is performed in order to provide what is usually the primary treatment of respiration to the child. The AHA recommends a ratio 15 chest compressions to two ventilations in the case of an adult victim and a ratio of five chest compressions to one ventilation in the case of pediatric victims. The recommended rate of compressions in both adult and pediatric victims is 100 compressions per minute. The rationale for this difference in compression to ventilation ratios is that: 1) the most common cause in pediatric (<8 years of age) arrest is respiratory; and 2) respiratory rates in pediatric (<8 years of age) population are faster than respiratory rates in adults. In addition, the recommended depth of chest compression for pediatric victims (<8 years of age) is 1 to 1.5 inches while the recommended chest compression depth for adult and pediatric (>8 years of age) is 1.5 to 2 inches.

Existing AEDs are unable to provide appropriate rescue protocol and ECG analysis for a pediatric (<8 years of age) victim that is different from an adult rescue protocol and ECG analysis. Also, a lay rescuer who is trained on pediatric resuscitation and is not aware of the AHA guidelines recommendations will not be able to provide an effective resuscitation for a pediatric victim when using these existing AEDs.

SUMMARY

In a first aspect, the invention features a device for assisting a rescuer in delivering therapy to an adult or pediatric patient, the device comprising a user interface comprising a display and/or audio speakers, the user interface being configured to deliver prompts to a rescuer to assist the rescuer in delivering therapy to a patient, a processor configured to provide prompts to the user interface and to perform an ECG analysis algorithm on ECG information detected from the patient, at least one detection element configured to determine without rescuer input via the user interface that a pediatric patient is being treated, wherein if a pediatric patient is detected, the processor modifies the ECG analysis algorithm to use an ECG analysis algorithm configured for a pediatric patient rather than for an adult patient.

In a second aspect, the invention features a device for assisting a rescuer in delivering therapy to an adult or pediatric patient, the device comprising a user interface comprising a display and/or audio speakers, the user interface being configured to deliver prompts to a rescuer to assist the rescuer in delivering therapy to a patient, a processor configured to provide prompts to the user interface and to perform an ECG analysis algorithm on ECG information detected from the patient, at least one detection element configured to determine without rescuer input via the user interface that a pediatric patient is being treated, wherein if a pediatric patient is detected, the processor modifies the prompts provided to the user interface to use prompts adapted for a pediatric patient rather than for an adult patient.

In a third aspect, the invention features a device for assisting a rescuer in delivering therapy to an adult or pediatric patient, the device comprising a user interface comprising a display and/or audio speakers, the user interface being configured to deliver prompts to a rescuer to assist the rescuer in delivering therapy to a patient, a processor configured to provide prompts to the user interface and to perform an ECG analysis algorithm on ECG information detected from the patient, at least one detection element configured to determine without rescuer input via the user interface that a pediatric patient is being treated, wherein if a pediatric patient is detected, the processor modifies the CPR protocol that governs CPR prompts provided to the user interface to use CPR prompts adapted for a pediatric patient rather than for an adult patient.

In preferred implementations, one or more of the following features may be incorporated. The invention may further comprise an automatic external defibrillator for delivering defibrillation shocks to the patient using defibrillation electrodes applied to the patient. The prompts provided via the user interface may comprise prompts as to CPR chest compression, and the CPR chest compression prompts may be changed from an adult set of prompts to a pediatric set of prompts if a pediatric patient is detected. The pediatric set of prompts may address depth and rate of CPR chest compressions. The invention may further comprise one or more sensors for measuring the rate and depth of CPR related chest compressions. The detection element may comprise circuitry for detecting whether a pediatric or an adult defibrillation electrode is in use. The detection element may comprise a force or pressure sensor located on a shoulder support element for sensing force or pressure from the weight of the patient. The energy of defibrillation shocks may be determined based in part on information as to the patient's weight obtained from the force or pressure sensor on the shoulder support. The shoulder support element may comprise a removable cover of the device. The detection element may comprise one or more sensors for determining from the separation of defibrillation electrodes placed on the patient whether the patient is a pediatric or adult patient.

In a fourth aspect, the invention features an external defibrillation device for assisting a rescuer in delivering defibrillation therapy to an adult or pediatric patient, the device comprising a user interface comprising a display or audio speakers, the user interface being configured to deliver prompts to a rescuer to assist the rescuer in delivering therapy to a patient, a processor configured to provide prompts to the user interface and to perform an ECG analysis algorithm on ECG information detected from the patient, a force or pressure sensor for detecting information pertaining to the weight of the patient, wherein the processor modifies the defibrillation energy delivered to the patient based on the information pertaining to the weight of the patient.

In preferred implementations, one or more of the following features may be incorporated. The processor may modify the ECG analysis algorithm based on the information pertaining to the weight of the patient. The force or pressure sensor may be incorporated into a shoulder support that is placed under the shoulders of the patient. The shoulder support may be a cover for the defibrillator. The cover may have an upper surface that is inclined at an angle that makes it suitable to be used to properly position the patient's airway by lifting the patient's shoulders to cause the patient's head to tilt back at an angle. The cover may be configured to be positioned under a patient's neck and shoulders to support the patient's shoulders and neck in a way that helps to maintain the patient's airway in an open position. The information from sensors in the shoulder support element may be communicated to the defibrillator by one or more of the following techniques: by a wire extending from the support to the defibrillator, or by a wireless communication connection between the support and the defibrillator.

In a fifth aspect, the invention features an external defibrillation device for assisting a rescuer in delivering defibrillation therapy to an adult or pediatric patient, the device comprising a user interface comprising a display or audio speakers, the user interface being configured to deliver prompts to a rescuer to assist the rescuer in delivering therapy to a patient, a processor configured to provide prompts to the user interface and to perform an ECG analysis algorithm on ECG information detected from the patient, a shoulder support element for placement under the shoulders of the patient to assist in keeping the airway open, sensors in the shoulder support element for determining if the patient's shoulders have been properly positioned on the element.

In preferred implementations, one or more of the following features may be incorporated. The shoulder support element may comprise a cover for the device.

In a sixth aspect, the invention features an external defibrillation device for assisting a rescuer in delivering defibrillation therapy to an adult or pediatric patient, the device comprising a user interface comprising a display or audio speakers, the user interface being configured to deliver prompts to a rescuer to assist the rescuer in delivering therapy to a patient, a processor configured to provide prompts to the user interface and to perform an ECG analysis algorithm on ECG information detected from the patient, defibrillation electrodes for placement on the chest of the patient, one or more sensors located in one or both of the defibrillation electrodes, the sensors being configured to determine a distance between the electrodes after they are placed on the patient's chest, wherein the processor can determine information pertaining to the size of the patient from the distance determined from the one or more sensors, and wherein the processor can vary the prompts, or the ECG analysis algorithm, or the energy delivered to the patient based on the information pertaining to the size of the patient.

In preferred implementations, one or more of the following features may be incorporated. The processor may estimate the circumferential girth of the patient from the information obtained from the sensors. The processor may estimate the age of the patient from the information obtained from the sensors. Modifications to the ECG analysis algorithm may include one or more of the following: heart rate criteria, QRS width criteria, VF frequency content criteria, or ECG amplitude criteria. Modifications to the prompts may include changing a sequence of prompts, a number of prompts, or a type of prompts. The prompts may include prompts on CPR compression and CPR ventilation, and the compression-ventilation ratio may be about 5:1 for pediatric patients and about 15:2 for adult patients. The prompts may include prompts on CPR compression depth, and the desired compression depth for pediatric patients may be in the range of about 1.0 to 1.5 inches, and the desired compression depth for adult patients may be in the range of about 1.0 to 2.0 inches. The prompts may include a prompt informing the rescuer as to whether the device is operating in an adult or pediatric mode. The prompts may include prompting of the CPR interval T1 based on one or more of patient rhythm, age, or weight. The invention may further comprise one or more sensors and prompts for detecting and prompting the user to achieve a complete chest release during CPR. The prompts may include pediatric specific prompts for the compression rate R1. The prompts may include adult specific prompts for the compression rate R1.

The invention may feature a system that will alter the AED arrhythmia processing for adults or children based the automatic sensing or manual assignment of the patient type.

Altering the AED arrhythmia processing for pediatric subjects based on the pediatric specific logic may achieve higher sensitivity and specificity of the shock decision that will significantly improve the safety and effective of the device.

The invention may provide an improved method for providing an appropriate rescue protocol and ECG analysis based on patient age, thoracic circumferential girth and weight in an automated fashion without the need for any user intervention. Utilizing a means of detecting a patient's age, weight or thoracic circumferential girth, the AED can automatically switch to providing the appropriate rescue protocol and optimizing performance of the ECG analysis algorithm for a specific victim age and weight. If an untrained rescuer activates the proposed AED, the protocol is tailored to instruct the user to provide one minute of CPR to the pediatric (<8 years of age) victim before activating the EMS system. The protocol is tailored to instruct the user to activate the EMS system before providing any treatment or CPR to an adult victim. Also, since the AED is capable of detecting the depth of chest compression when used with a set of defibrillation electrodes embedding a chest compression detector, it can guide the rescuer to administer appropriate chest compression-ventilation ratio and depth of compressions based on specific victim age and weight. Furthermore, the proposed AED can select a preconfigured CPR period length based on the type of rhythm when the CPR interval is entered. For example, the pre-programmed CPR period when an asystole, PEA, or normal rhythm is detected can be longer than after a ventricular fibrillation or tachycardia is detected.

The invention may provide a more comprehensive and effective system for delivering treatment to pediatric arrest victims, providing an appropriate rescue protocol and ECG analysis based on patient age, thoracic circumferential girth and weight in an automated fashion without the need for any user intervention.

The invention may feature a device for assisting a rescuer in delivering therapy to an adult or pediatric patient, the device comprising a user interface comprising a display or audio speakers, the user interface being configured to deliver prompts to a rescuer to assist the rescuer in delivering therapy to a patient; a processor configured to provide prompts to the user interface and to perform an ECG analysis algorithm on ECG information detected from the patient; at least one detection element configured to determine without rescuer input via the user interface that a pediatric patient is being treated; wherein, if a pediatric patient is detected, the processor modifies the ECG analysis algorithm or the prompts provided to the user interface to use an ECG analysis algorithm or prompts better suited to a pediatric patient than to an adult patient.

The device may incorporate an automatic external defibrillator for delivering defibrillation shocks to the patient using defibrillation electrodes applied to the patient. The prompts provided via the user interface may comprise prompts as to CPR chest compression, and the CPR chest compression prompts are changed from an adult set of prompts to a pediatric set of prompts if a pediatric patient is detected. The pediatric set of prompts may address depth and rate of CPR chest compressions. One or more sensors for measuring the rate and depth of CPR related chest compressions may be provided. The detection element may comprise circuitry for detecting whether a pediatric or an adult defibrillation electrode is in use. The detection element may comprise a force or pressure sensor located on a shoulder support element for sensing force or pressure from the weight of the patient. The energy of defibrillation shocks may be determined based in part on information as to the patient's weight obtained from the force or pressure sensor on the shoulder support. The shoulder support element may comprise a removable cover of the device. The detection element may comprise one or more sensors for determining from the separation of defibrillation electrodes placed on the patient whether the patient is a pediatric or adult patient.

The AED may include the capability of measuring the rate and depth of CPR related chest compressions and automatically switch when specific defibrillation electrode types are detected to provide appropriate rescue protocol, ECG analysis, and CPR interval length and guidance based on the victim's determined age. Based on the determined patient age, appropriate ventilation to compression ratio and compression interval length are determined, and guidance is provided to the rescuer to provide appropriate chest compressions/ventilation ratio and rate and compression depth via voice and text prompts throughout the entire rescue process.

The invention may feature an external defibrillation device for assisting a rescuer in delivering defibrillation therapy to an adult or pediatric patient. The device may comprise a user interface comprising a display or audio speakers, the user interface being configured to deliver prompts to a rescuer to assist the rescuer in delivering therapy to a patient; a processor configured to provide prompts to the user interface and to perform an ECG analysis algorithm on ECG information detected from the patient; a force or pressure sensor for detecting information pertaining to the weight of the patient; wherein the processor modifies the defibrillation energy delivered to the patient based on the information pertaining to the weight of the patient.

The processor may modify the ECG analysis algorithm based on the information pertaining to the weight of the patient. The force or pressure sensor may be incorporated into a shoulder support that is placed under the shoulders of the patient. The shoulder support may be a cover for the defibrillator. The cover may have an upper surface that is inclined at an angle that makes it suitable to be used to properly position the patient's airway by lifting the patient's shoulders to cause the patient's head to tilt back at an angle. The cover may be configured to be positioned under a patient's neck and shoulders to support the patient's shoulders and neck in a way that helps to maintain the patient's airway in an open position. The information from sensors in the shoulder support element may be communicated to the defibrillator by one or more of the following techniques: by a wire extending from the support to the defibrillator, or by a wireless communication connection between the support and the defibrillator.

Some implementations may provide an automated means for determining the age of the victim with greater specificity. Victim weight is a commonly used clinical measure for determining defibrillation energies for children. An integrated force sensor may be provided within the AED for measuring the patient's weight and the AED will then adjust the defibrillation energy and ECG analysis parameters based on the measured weight.

The force sensor may be incorporated into the cover of the AED. The cover has an upper surface that is inclined at an angle that makes it suitable to be used to properly position the patient's airway, by, for instance, lifting the patient's shoulders thereby causing the patient's head to tilt back at the proper angle. The cover is constructed to be positioned under a patient's neck and shoulders to support the patient's shoulders and neck in a way that helps to maintain his airway in an open position, i.e., maintaining the patient in the head tuck-chin lift position. When a caregiver encounters a person who appears to be suffering from cardiac arrest, the caregiver should follow recommended resuscitation procedures, such as are specified by the AHA Guidelines for Cardiopulmonary Resuscitation and Emergency Cardiovascular Care. If there is no evidence of head or neck trauma, the caregiver should clear any debris from the patient's airway. After this has been done, the caregiver should roll the patient onto his side, place cover under the patient's shoulders, and roll the patient back onto his back. The cover should be positioned so as to support the patient in the head tilt-chin lift position. The caregiver can then proceed with CPR and/or use of the defibrillator. The positions (a patient in the head lift-chin tilt position and a patient with a closed airway) are also shown in the AHA Guidelines for Cardiopulmonary Resuscitation and Emergency Cardiovascular Care, Aug. 22, 2000, p. I-32, FIGS. 7 and 8. The cover is provided with a detection means for determining if the patient's shoulders have been properly positioned on the cover. Communication of the detection means located in the cover to the processor in the device housing can be accomplished by making the cover an integral element of the device housing, for instance via a hinge element or by providing an interconnection element such as a flat flexible cable. Communication may also be accomplished wirelessly via such technologies as Bluetooth or inductive methods. When the patient's shoulders are placed on the cover, the measured force is communicated to the AED.

The invention may feature an external defibrillation device for assisting a rescuer in delivering defibrillation therapy to an adult or pediatric patient, the device comprising a user interface comprising a display or audio speakers, the user interface being configured to deliver prompts to a rescuer to assist the rescuer in delivering therapy to a patient; a processor configured to provide prompts to the user interface and to perform an ECG analysis algorithm on ECG information detected from the patient; a shoulder support element for placement under the shoulders of the patient to assist in keeping the airway open; sensors in the shoulder support element for determining if the patient's shoulders have been properly positioned on the element.

The invention may feature an external defibrillation device for assisting a rescuer in delivering defibrillation therapy to an adult or pediatric patient, the device comprising a user interface comprising a display or audio speakers, the user interface being configured to deliver prompts to a rescuer to assist the rescuer in delivering therapy to a patient; a processor configured to provide prompts to the user interface and to perform an ECG analysis algorithm on ECG information detected from the patient; defibrillation electrodes for placement on the chest of the patient; one or more sensors located in one or both of the defibrillation electrodes, the sensors being configured to determine a distance between the electrodes after they are placed on the patient's chest; wherein the processor can determine information pertaining to the size of the patient from the distance determined from the one or more sensors, and wherein the processor can vary the prompts, or the ECG analysis algorithm, or the energy delivered to the patient based on the information pertaining to the size of the patient.

The processor may estimate the circumferential girth of the patient from the information obtained from the sensors. The processor may estimate the age of the patient from the information obtained from the sensors.

The sensor elements may be fabricated into the two defibrillation electrodes placed on the victim's chest. The electrodes may be constructed such that the relative distance between the electrodes can be determined by the AED. Based on that relative distance, the circumferential girth can be calculated by the AED and used as a means of estimating patient age as well as delivering the appropriate energy level.

Other features and advantages of the invention will be apparent from the description and drawings, and from the claims.

DESCRIPTION OF DRAWINGS

FIG. 1 is a perspective view of an AED with its cover on.

FIG. 15 is an example AED arrhythmia logic table for an adult.

FIG. 16 is an example AED arrhythmia logic table for a child.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

The terms "caregiver", "rescuer" and "user" are used interchangeably in the description of the invention and refer to the operator of the device providing care to the patient. "Victim" is also used interchangeably with "patient".

Figure 1:
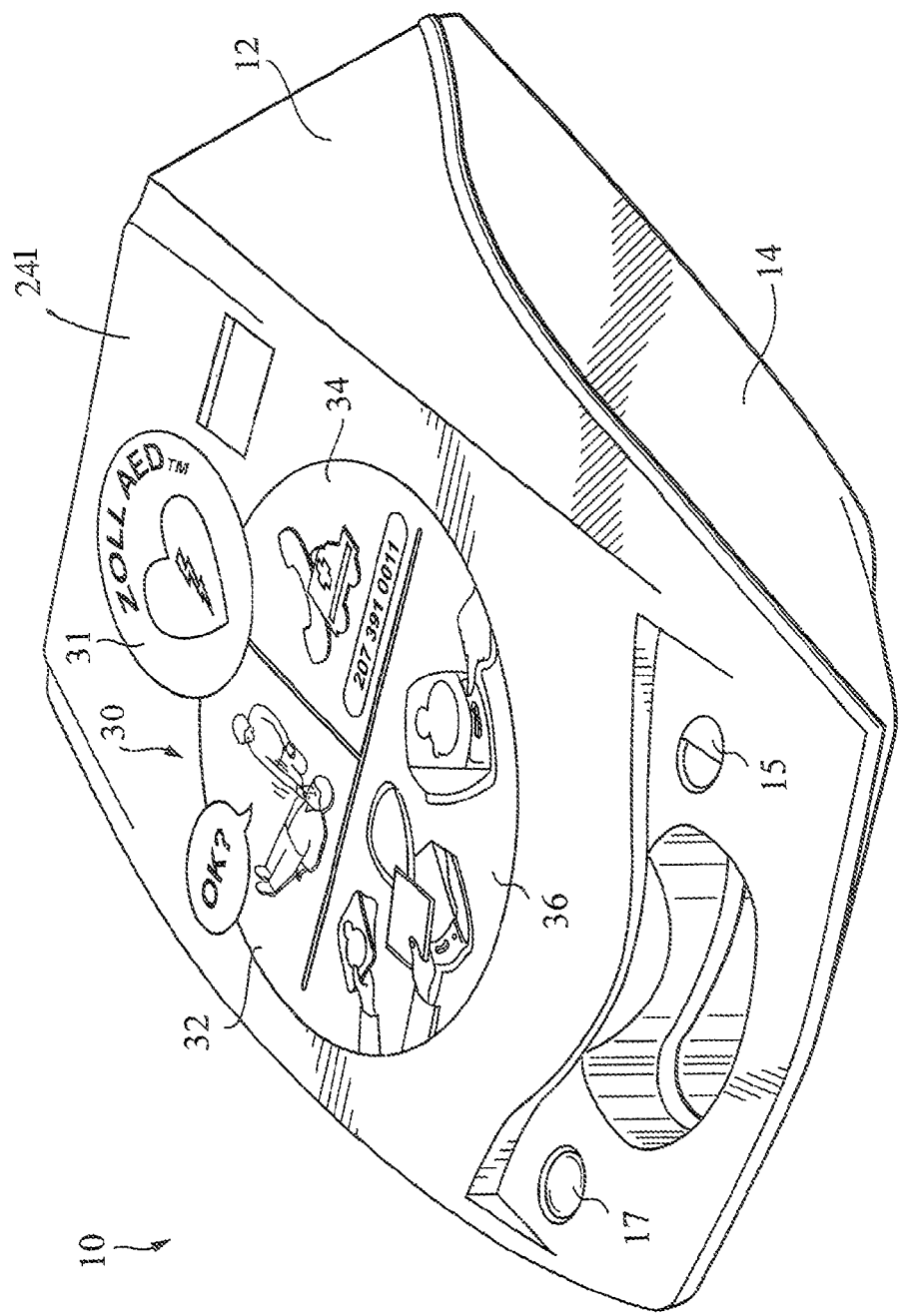
Figure 2:
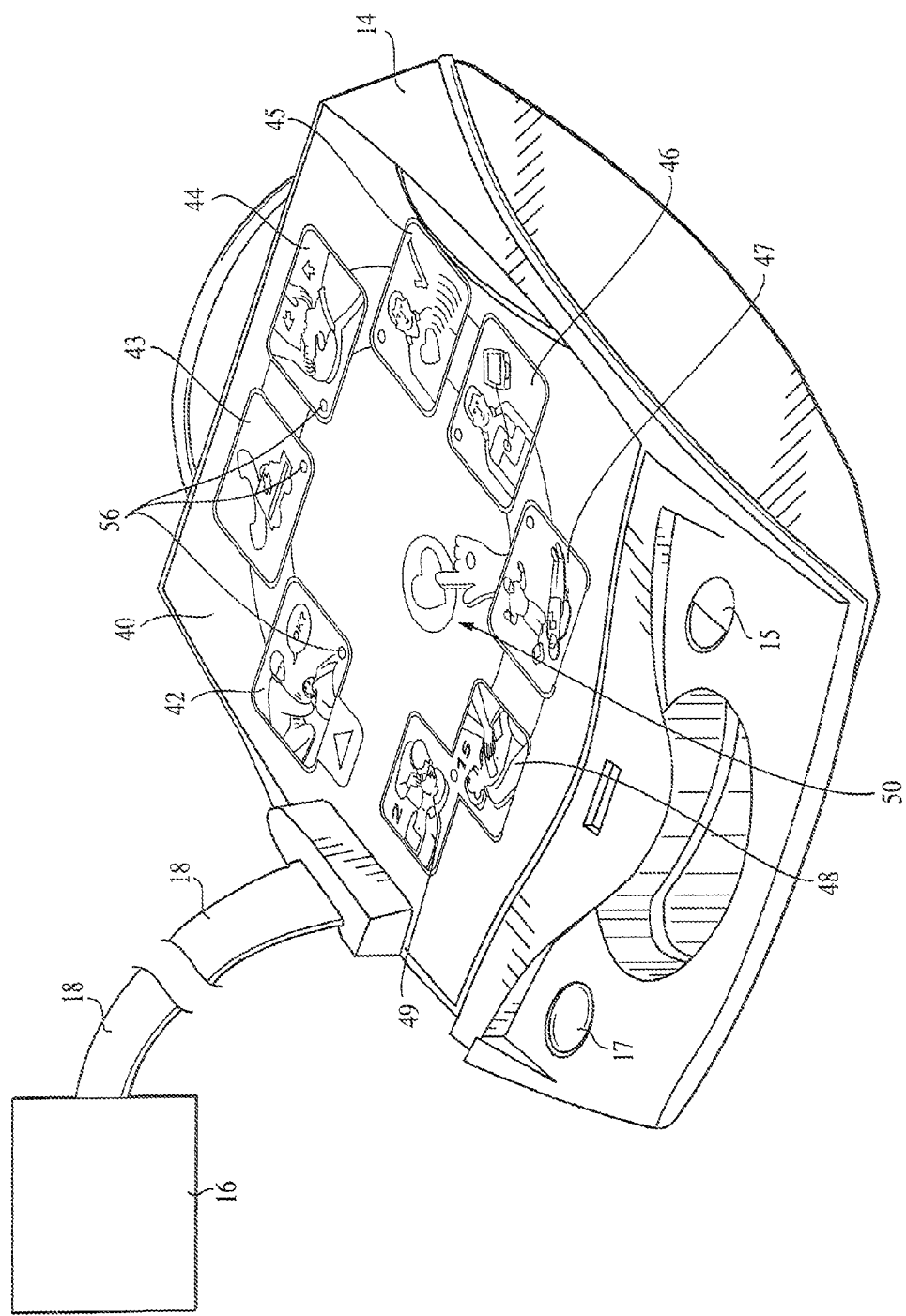
FIG. 2 is a perspective view of the AED of FIG. 1 with the cover removed.

Referring to FIGS. 1 and 2, an automated external defibrillator 10 includes a removable cover 12 and a device housing 14. The defibrillator 10 is shown with cover 12 removed in FIG. 2. An electrode assembly 16 (or a pair of separate electrodes) is connected to the device housing 14 by a cable 18. Electrode assembly 16 is stored under cover 12 when the defibrillator is not in use.

Figure 3:
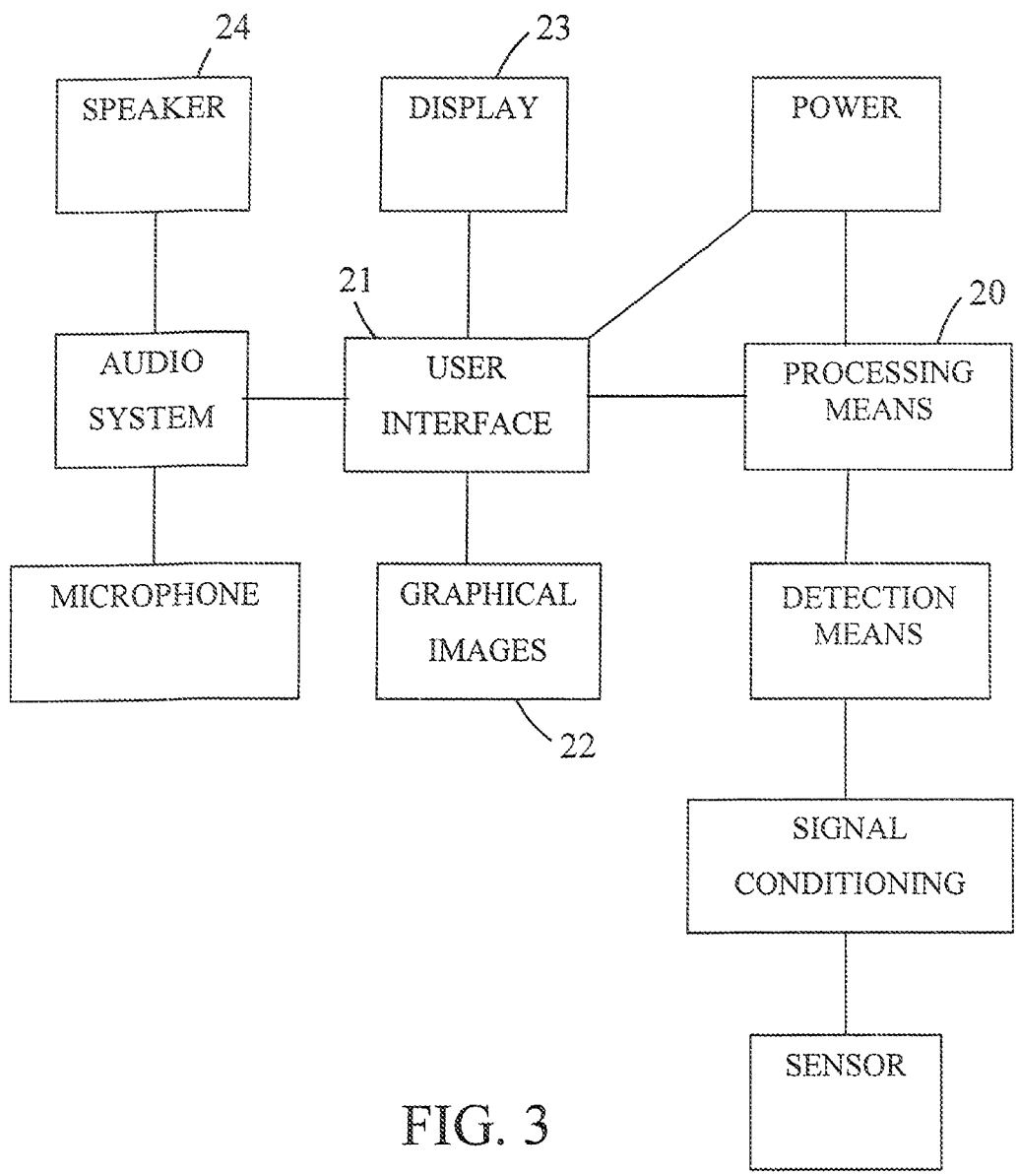
FIG. 3 is a block diagram of the AED.

Referring to FIG. 3, the invention includes a processor means 20, a user interface 21 including such elements as a graphical 22 or text display 23 or an audio output such as a speaker 24, and a detection means for determining whether at least one of a series of steps in a protocol has been completed successfully. In the preferred embodiment, the detection means also includes the ability to determine both whether a particular step has been initiated by a user and additionally whether that particular step has been successfully completed by a user. Based on usability studies in either simulated or actual use, common user errors are determined and specific detection means are provided for determining if the most prevalent errors have occurred.

Device housing 14 includes a power button 15 and a status indicator 17. Status indicator 17 indicates to the caregiver whether the defibrillator is ready to use.

Figure 4:
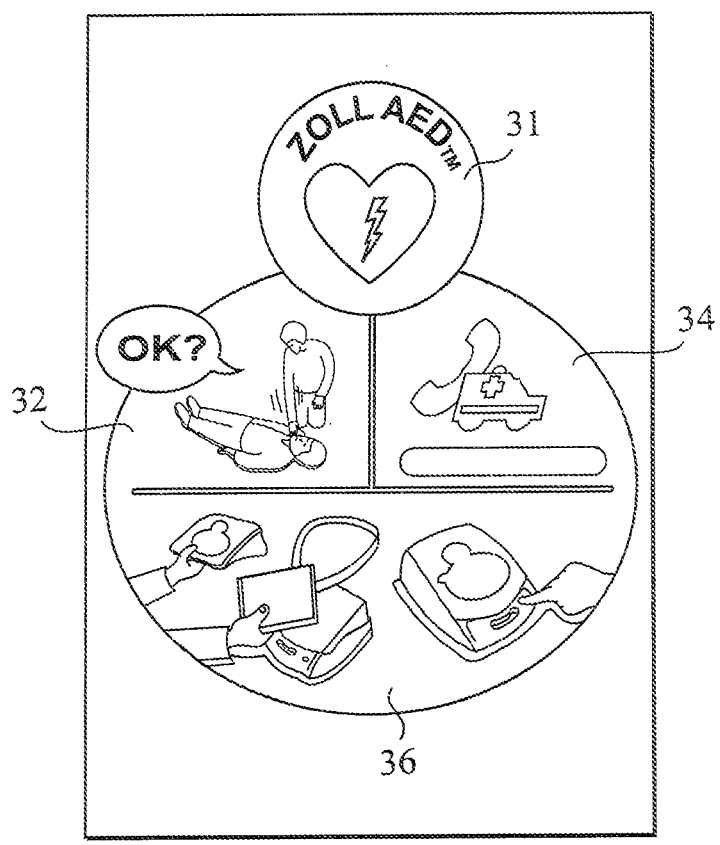
FIG. 4 is a plan view of the graphical interface decal used on the cover of the AED of FIG. 1.

The cover 12 includes a cover decal 30 (FIGS. 1 and 4) including a logo 31 and a series of graphics 32, 34 and 36. Logo 31 may provide information concerning the manufacturer of the device and that the device is a defibrillator (e.g., "ZOLL AED", as shown in FIG. 1, indicating that the device is a Semi-automatic External Defibrillator available from ZOLL Medical). Graphics 32, 34 and 36 lead the caregiver through the initial stages of a cardiac resuscitation sequence as outlined in the AHA's AED treatment algorithm for Emergency Cardiac Care pending arrival of emergency medical personnel. (See "Guidelines 2000 for Cardiopulmonary Resuscitation and Emergency Cardiovascular Care. Supplement to Circulation," Volume 102, Number 8, Aug. 22, 2000, pp. 1-67.) Thus, graphic 32, showing the caregiver and patient, indicates that the caregiver should first check the patient for responsiveness, e.g., by shaking the patient gently and asking if the patient is okay. Next, graphic 34, showing a telephone and an emergency vehicle, indicates that the caregiver should call for emergency assistance prior to administering resuscitation. Finally, graphic 36 indicates that after these steps have been performed the caregiver should remove the cover 12 of the defibrillator, remove the electrode assembly 16 stored under the lid, and turn the power on by depressing button 15. The graphics are arranged in clockwise order, with the first step in the upper left, since this is the order most caregivers would intuitively follow. However, in this case the order in which the caregiver performs the steps is not critical, and thus for simplicity no other indication of the order of steps is provided.

Figure 9A:
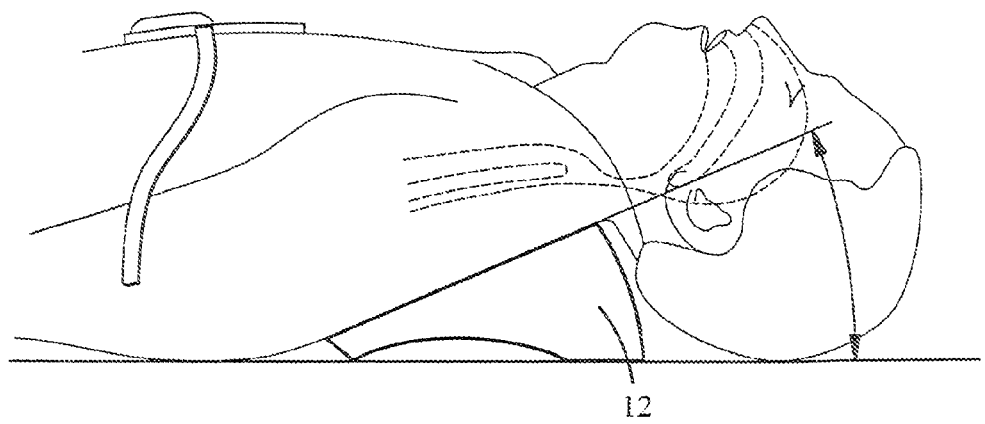
FIGS. 9a and 9b show the effect on the patient's airway of placing the cover beneath a patient's shoulders.
Figure 9B:
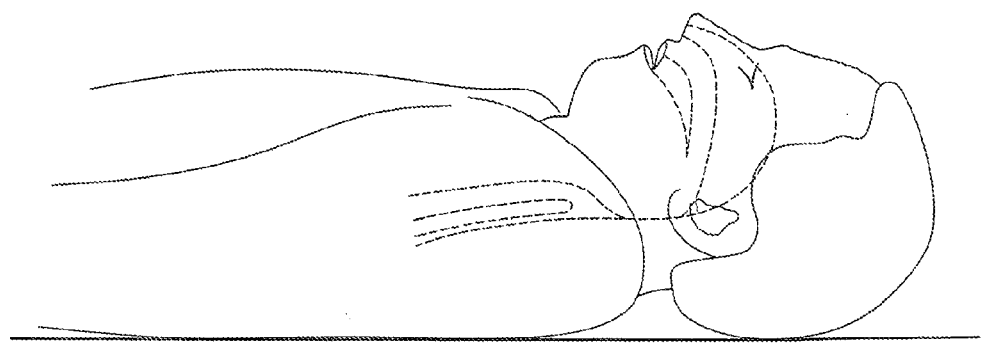

The cover 12 is constructed to be positioned under a patient's neck and shoulders, as shown in FIGS. 9a and 9b to support the patient's shoulders and neck in a way that helps to maintain his airway in an open position, i.e., maintaining the patient in the head tuck-chin lift position. The cover is preferably formed of a relatively rigid plastic with sufficient wall thickness to provide firm support during resuscitation. Suitable plastics include, for example, ABS, polypropylene, and ABS/polypropylene blends.

Prior to administering treatment for cardiac arrest, the caregiver should make sure that the patient's airway is clear and unobstructed, to assure passage of air into the lungs. To prevent obstruction of the airway by the patient's tongue and epiglottis (e.g., as shown in FIG. 9a), it is desirable that the patient be put in a position in which the neck is supported in an elevated position with the head tilted back and down. Positioning the patient in this manner is referred to in the American Heart Association Guidelines for Cardiopulmonary Resuscitation and Emergency Cardiovascular Care as the "head tilt-chin lift maneuver." The head tilt-chin lift position provides a relatively straight, open airway to the lungs through the mouth and trachea. However, it may be difficult to maintain the patient in this position during emergency treatment.

The cover 12 has an upper surface 241 that is inclined at an angle A (FIG. 8) of from about 10 to 25 degrees, e.g., 15 to 20 degrees, so as to lift the patient's shoulders and thereby cause the patient's head to tilt back. The upper surface 241 is smoothly curved to facilitate positioning of the patient. A curved surface, e.g., having a radius of curvature of from about 20 to 30 inches, generally provides better positioning than a flat surface. At its highest point, the cover 12 has a height H (FIG. 8) of from about 7.5 to 10 cm. To accommodate the width of most patients' shoulders, the cover 12 preferably has a width W (FIG. 8) of at least 6 inches, e.g., from about 6 to 10 inches. If the cover 12 is not wide enough, the patient's neck and shoulders may move around during chest compressions, reducing the effectiveness of the device. The positions shown in FIGS. 9a and 9b (a patient in the head lift-chin tilt position and a patient with a closed airway) are also shown in the AHA Guidelines for Cardiopulmonary Resuscitation and Emergency Cardiovascular Care, Aug. 22, 2000, p. I-32, FIGS. 7 and 8.

Figure 6A:
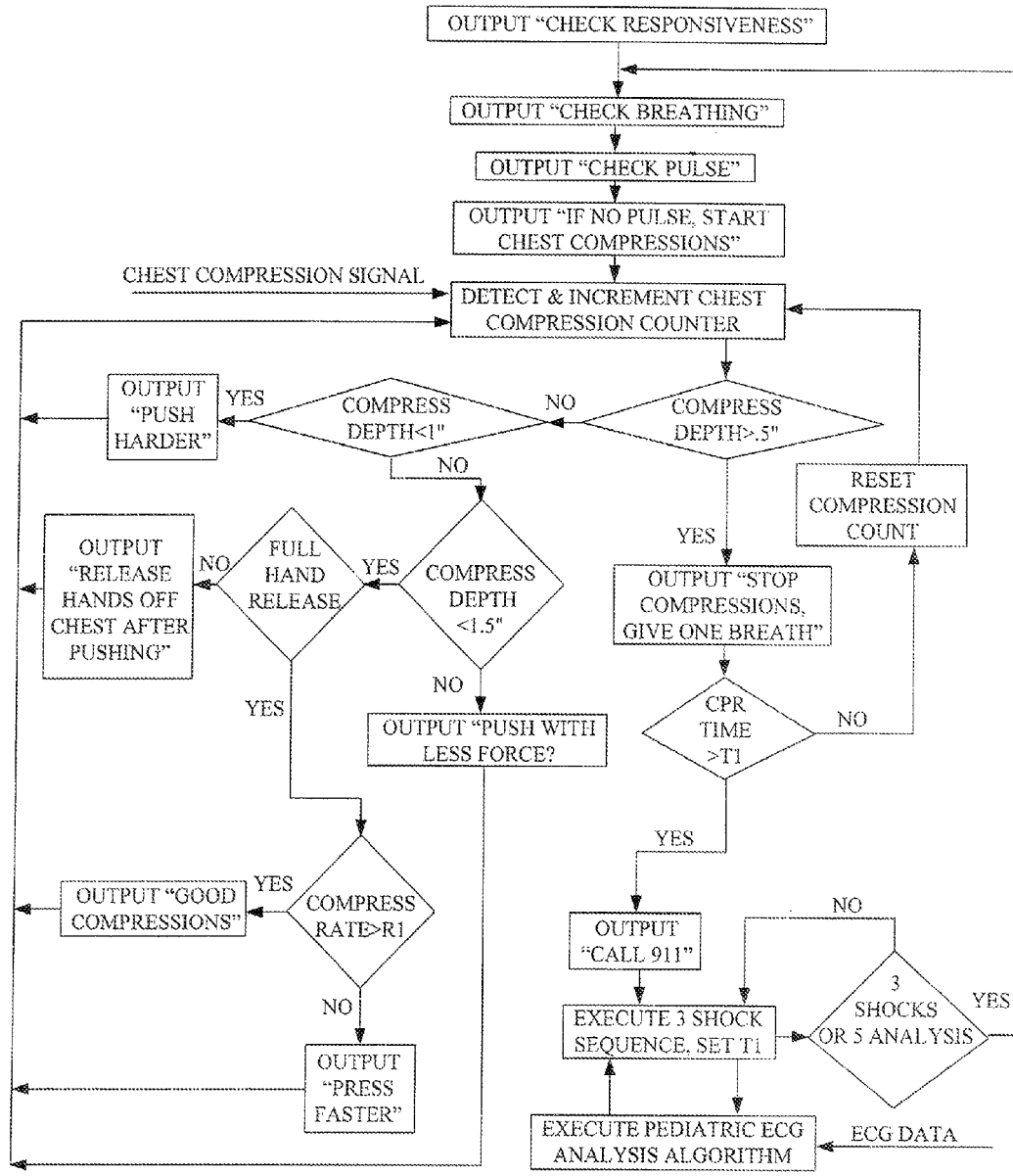
FIG. 6a is a flow diagram for the pediatric AED resuscitation protocol.

In a preferred implementation, if on power-up, the AED detects that the pediatric defibrillation pads are attached then the AED will automatically start a pediatric rescue protocol. FIG. 6a shows the details of one instance of the pediatric protocol. The device will output voice/text prompts indicating to the rescuer to check the victim's responsiveness (i.e., "Check Responsiveness") and allow a preprogrammed time interval (e.g., 4 seconds) to allow for checking the responsiveness before moving to the next state. The device will next output voice/text prompts instructing the rescuer to check breathing (example "Check Breathing") and then allow a preprogrammed time interval (e.g., 7 seconds) to check the victim's breathing. The AED will next output voice/text prompts instructing the rescuer to check the victim's pulse (example "Check Pulse") and then allow a preprogrammed time interval (e.g., 10 sec) for checking the victim's pulse. The AED will then enter a CPR state where it outputs voice/text prompts instructing the rescuer to start chest compressions (e.g., "If No Pulse, Start Chest Compressions"). While in this CPR state, the chest compression signal is received by 'Detect & Increment Chest Compressions Counter' function that detects chest compressions and counts them. While the number of chest compressions is less than 5, the depth of each detected compression is evaluated. If the depth of the detected compression is not higher than 1", the rescuer is instructed to push harder on the victims chest by outputting "Push Harder" voice/text prompts and return to 'Detect & Increment Chest Compression count' state. Else, if the depth of the detected chest compression exceeds 1", this depth is evaluated again. If the depth of the detected compression is less than 1.5", a check is made for complete hand release to allow the victim's chest to recoil. If the rescuer hand is released off the victim chest after every compression, then the AED checks if the compression rate is higher than a preprogrammed R1 rate. If the compression rate is higher than R1, the AED output voice/text prompts indicating effective compressions "Good Compressions". Else, the compression rate is less than R1, the AED output voice/text prompts instructing the rescuer to press faster and return to 'Detect & Increment Chest Compression count' state.

If the rescuer is not releasing the hands off the chest after each compression, the AED instructs the user to release the hands off the victim's chest after each compression by outputting voice/text prompts "Release Hands Off Chest After Pushing", then returns to 'Detect & Increment Chest Compressions Count' state. If the depth of the detected chest compression is greater than 1.5", the AED instructs the rescuer to push on the victim chest with less force by outputting the prompt "Push With Less Force", then returns to 'Detect & Increment Chest Compressions Count' state. If the number of chest compressions exceeds 5, the device instructs the rescuer to stop compressions and give the victim one breath by outputting voice/text prompts "Stop Compressions, Give One Breath", then checks if the CPR state time interval exceeds a timer T1. If CPR state time interval is less than T1, the chest compression counter is reset and the AED returns to 'Detect & Increment Chest Compressions Count' state. If the CPR state time interval exceeds T1, the AED instructs the rescuer to activate the EMS system by calling 911 and then the AED transitions to 'Execute 3 Shock Sequence, Set T1' state. In this state, the "Pediatric ECG Analysis Algorithm" is executed. If the first analysis detects a non-shockable rhythm, the AED transitions to the CPR state for another cycle of CPR. Else, if the first analysis detects a shockable rhythm, the rescuer is advised to deliver a defibrillation shock. Following the shock delivery a second analysis is automatically initiated to determine whether the defibrillation treatment was successful or not (i.e. the shockable ECG rhythm has been converted to a normal or other non-shockable rhythm). If this second analysis detects the continuing presence of a shockable arrhythmia, the AED advises the user to deliver a second defibrillation treatment.

A third ECG analysis is automatically initiated to determine whether the second shock was or was not effective. If a shockable rhythm persists, the rescuer is then advised to deliver a third defibrillation treatment. Following the third defibrillator shock or when any of the analyses described above detects a non-shockable rhythm, the AED transitions to the CPR state for another cycle of chest compressions and ventilation. Also In the 'Execute 3 Shock Sequence, Set T1' state, T1 is set to a preprogrammed value based on the type of the detected rhythm: normal, asystole, non-conductive, ventricular tachycardia or ventricular fibrillation. For instance, the asystole and non-conductive rhythms may require longer CPR periods than 1 minute in such case the 'Execute 3 Shock Sequence, Set T1' task will set the T1 to a preprogrammed value appropriate for pediatric asystole or non-conductive rhythms that may be longer than one minute. In the case of an arrhythmia, the required CPR time may be only 1 minute in such case the 'Execute 3 Shock Sequence, Set T1' task will set the T1 to a preprogrammed value appropriate for pediatric arrhythmia rhythms that may be one minute. In the case of normal rhythm, the required CPR time may be only 1 minute in such case the 'Execute 3 Shock Sequence, Set T1' task will set the T1 to a preprogrammed value appropriate for pediatric rhythms that may be one minute or longer.

Figure 6B:
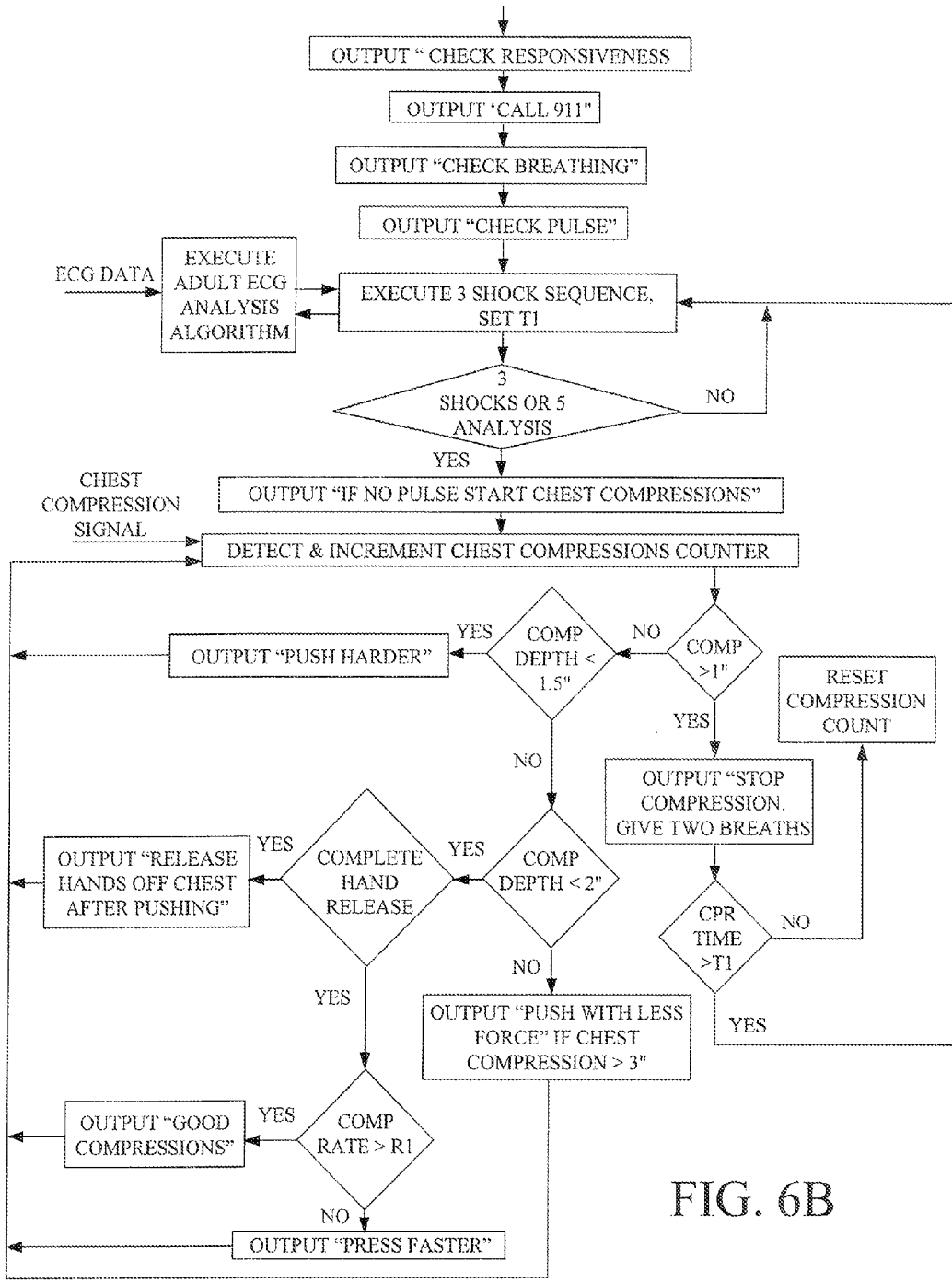
FIG. 6b is a flow diagram for the adult AED resuscitation protocol.

If on the other hand, the AED detects adult defibrillation pads on power-up, the AED will automatically start an adult rescue protocol. FIG. 6b shows the details of one instance of the adult rescue protocol. The AED will output voice/text prompts indicating to the rescuer to check the victim's responsiveness (i.e., "Check Responsiveness") and allow a preprogrammed time interval (i.e., 4 seconds) to expire to allow for checking the responsiveness before moving to the next state. Next, the AED instructs the rescuer to activate the EMS system by calling 911 and allow a preprogrammed time interval (e.g., 4 seconds) to expire to allow someone call for help before moving to the next state. The AED will next output voice/text prompts instructing the rescuer to check breathing (e.g., "Check Breathing") and then allow a preprogrammed time interval (example: 7 seconds) to check breathing. The device will next output voice/text prompts instructing the rescuer to check the victim's pulse (e.g., "Check Pulse") and then allow a preprogrammed time interval (e.g., 10 seconds) for the pulse check. The AED will then transitions to 'Execute 3 Shock Sequence, Set T1' state. In this state, the "Adult ECG Analysis Algorithm" is executed. If the first analysis detects a non-shockable rhythm, the AED will transition to the CPR state. Else, if the first analysis detects a shockable rhythm, the rescuer is advised to deliver a defibrillation shock.

Following the shock delivery a second analysis is automatically initiated to determine whether the defibrillation treatment was successful or not (i.e. the shockable ECG rhythm has been converted to a normal or other non-shockable rhythm). If this second analysis detects the continuing presence of a shockable arrhythmia, the AED advises the user to deliver a second defibrillation treatment. A third ECG analysis is automatically initiated to determine whether the second shock was or was not effective. If a shockable rhythm persists, the rescuer is then advised to deliver a third defibrillation treatment. Following the third defibrillator shock or when any of the analyses described above detects a non-shockable rhythm, the device transition to the CPR state for another cycle of CPR. Also In the 'Execute 3 Shock Sequence, Set T1 state, T1 is set to a preprogrammed value based on the type of the detected rhythm: normal, asystole, non-conductive, ventricular tachycardia or ventricular fibrillation. For instance, the asystole and non-conductive rhythms may require longer CPR periods than 1 minute in such case the 'Execute 3 Shock Sequence, Set T1' task will set the T1 to a preprogrammed value appropriate for adult asystole or non-conductive rhythms that may be longer than one minute. In the case of an arrhythmia, the required CPR time may be only 1 minute in such case the 'Execute 3 Shock Sequence, Set T1 task will set the T1 to a preprogrammed value appropriate for adult arrhythmia rhythms that may be one minute. In the case of normal rhythm, the required CPR time may be only 1 minute in such case the 'Execute 3 Shock Sequence, Set T1 task will set the T1 to a preprogrammed value appropriate for adult rhythms that may be one minute or longer. Upon entering the CPR state, the AED outputs voice/text prompts instructing the rescuer to start chest compressions (example "If No Pulse, Start Chest Compressions"). While in this CPR state the chest compression signal is received by 'Detect & Increment Chest Compressions Counter' function that detects chest compressions and counts them. While the number of chest compressions is less than 15, the depth of each detected compression is evaluated. If the depth of the detected compression is not higher than 1.5", the rescuer is instructed to push harder on the victims chest by outputting "Push Harder" voice/text prompts and return to 'Detect & Increment Chest Compression count' state. Else, if the depth of the detected chest compression exceeds 1.5", this depth is evaluated again. If the depth of the detected compression is less than 2", a check is made for complete hand release. If the rescuer hand is released off the victim chest after every compression to allow for complete chest recoil, then the AED checks if the compression rate is higher than a preprogrammed R1 rate. If the compression rate is higher than R1, the AED output voice/text prompts indicating effective compressions "Good Compressions". Else, the compression rate is less than R1, the AED output voice/text prompts instructing the rescuer to press faster and return to 'Detect & Increment Chest Compression count' state.

If the rescuer is not releasing the hands off the chest after each compression, the device instructs the user to release the hands off the victim's chest after each compression to provide more effective CPR by outputting voice/text prompts "Release Hands Off Chest After Pushing", then returns to 'Detect & Increment Chest Compressions Count' state. If the depth of the detected chest compression is greater than 3", the device instructs the rescuer to push on the victim chest with less force by outputting the prompt "Push With Less Force", then checks if compression rate is higher than a preprogrammed R1 rate. If the compression rate is higher than R1, the AED output voice/text prompts indicating effective compressions. Else, the compression rate is less than R1, the AED output voice/text prompts instructing the rescuer to press faster. If the number of chest compressions exceeds 15, the device instructs the rescuer to stop compressions and give the victim two breaths by outputting voice/text prompts "Stop Compressions, Give Two Breaths", then checks if the CPR state time interval exceeds a selected timer T1.

If CPR state time interval is less than T1, the chest compression counter is reset and the device returns to 'Detect & Increment Chest Compressions Count' state. If the CPR state time interval exceeds T1, the AED will transition to 'Execute 3 Shock Sequence, Set T1 state.

Figure 12:
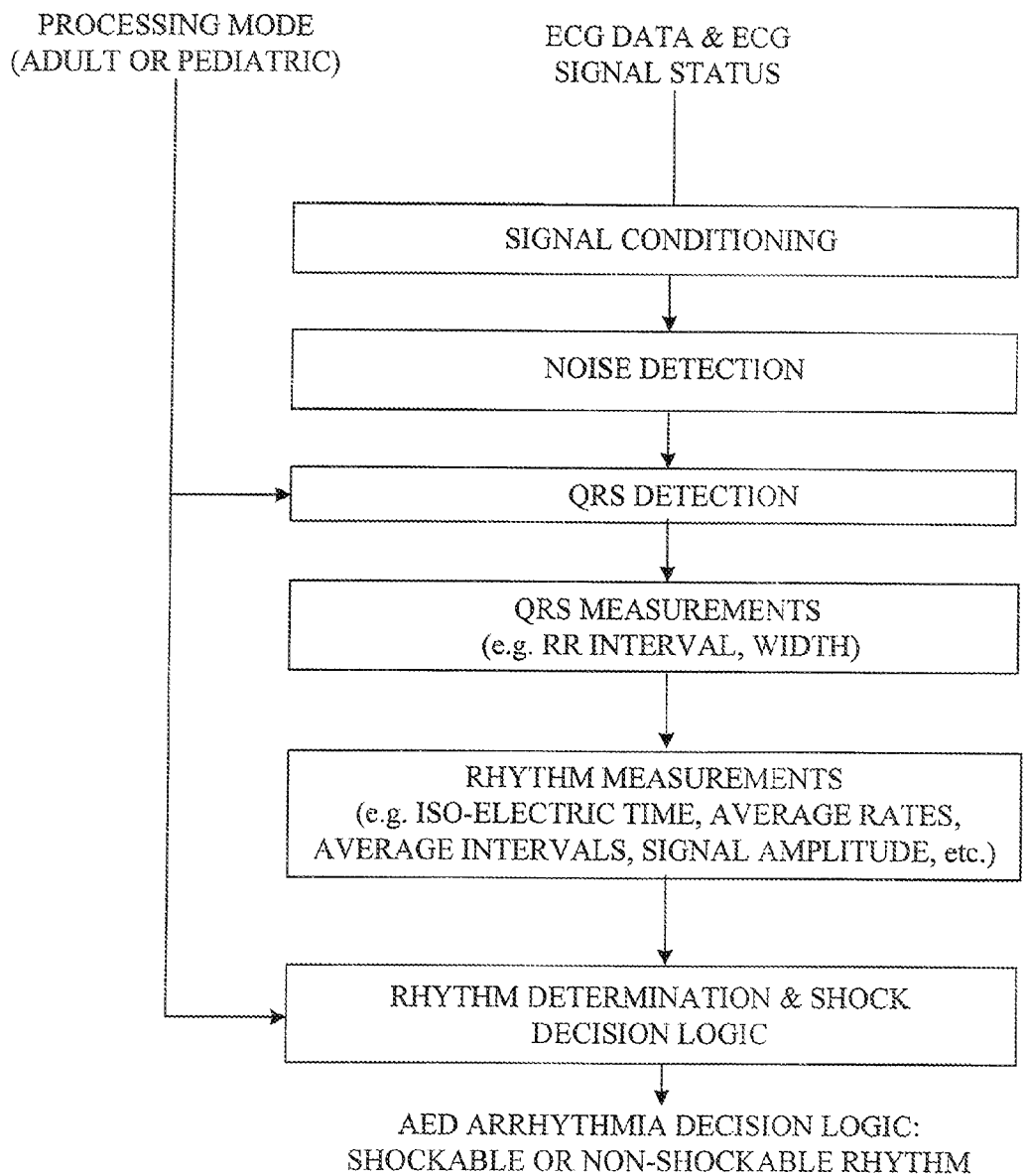
FIG. 12 is a flow diagram of the arrhythmia processing in the AED.

FIG. 12 shows an example of a AED Arrhythmia processing flow diagram. Since the pediatric QRS is narrower and the heart faster than adult, the QRS detection system can be tailored to be more sensitive to the ECG signal. The flow diagram also shows that the arrhythmia classification logic and shock decision logic can be altered to improve the specificity and sensitivity.

In the Signal Conditioning block, the ECG signal is band passed and notch filtered to remove baseline offsets, high frequency noise, and line noise frequency noise. The noise Detection block performs baseline, motion, high frequency, muscle, and saturation noise detections and flags the ECG Signal status data accordingly.

In the QRS detection block, the processing produces a QRS detection signal by performing a QRS based matched filter on the filtered ECG data. The type of processing performed is dependant on the Processing Mode Setting (reference FIG. 13).

Once the location of the QRS is detected in the signal stream, the QRS Detection Block will process the signal around the QRS detection to determine specific measurements such as R-R interval, QRS width, QRS area, and other features which will support classification of the QRS complex and its underlying rhythm. The Rhythm Measurement block will perform analysis on the QRS measures and ECG signal to produce rhythm based measures required for rhythm classification. The Rhythm Determination and Shock Determination Decision Logic block will process the QRS detection and rhythm data to classify the ECG rhythm and make a shock versus no shock decision. Many beat and rhythm classification techniques are know in the art and include heuristic logic, morphological analysis, expert system analysis, and statistical clustering techniques. The outputs from the Rhythm Determination and Shock Determination Decision Logic block are used by the AED to shock the victim (fully automatic AED) or notify the user to deliver a shock (semi-automatic AED) or begin other interventions such as CPR.

Figure 13:
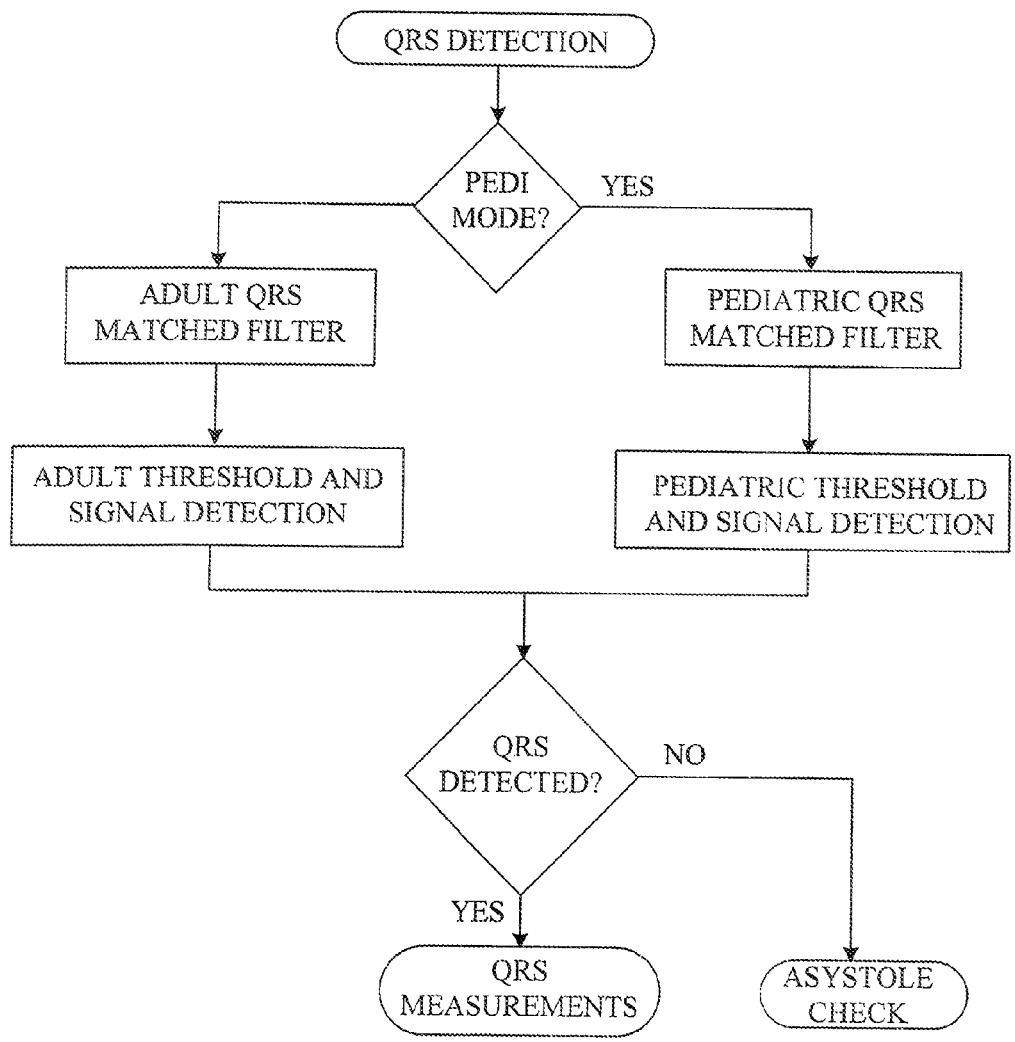
FIG. 13 is a flow diagram of mode specific processing for enhancing QRS detection.

FIG. 13 shows an example of the use of mode specific processing to enhance QRS detection. In the PEDI Mode selection block, the matched filter characteristics are chosen based on the Processing Mode setting (Adult or Pediatric) to produce an optimal detection signal for that class of patients. A threshold detection scheme is used to determine the location of the QRS complexes in the detection signal. A threshold system is utilized which has been optimized for use with the respective QRS matched filter. The QRS Detection Selection block determines whether to perform QRS Measurements (QRS Detected) or perform an Asystole Check (QRS Not Detected). The Asystole check will process a detection timeout, adjust detection thresholds, and notify the target system if an asystole state is present.

Figure 14:
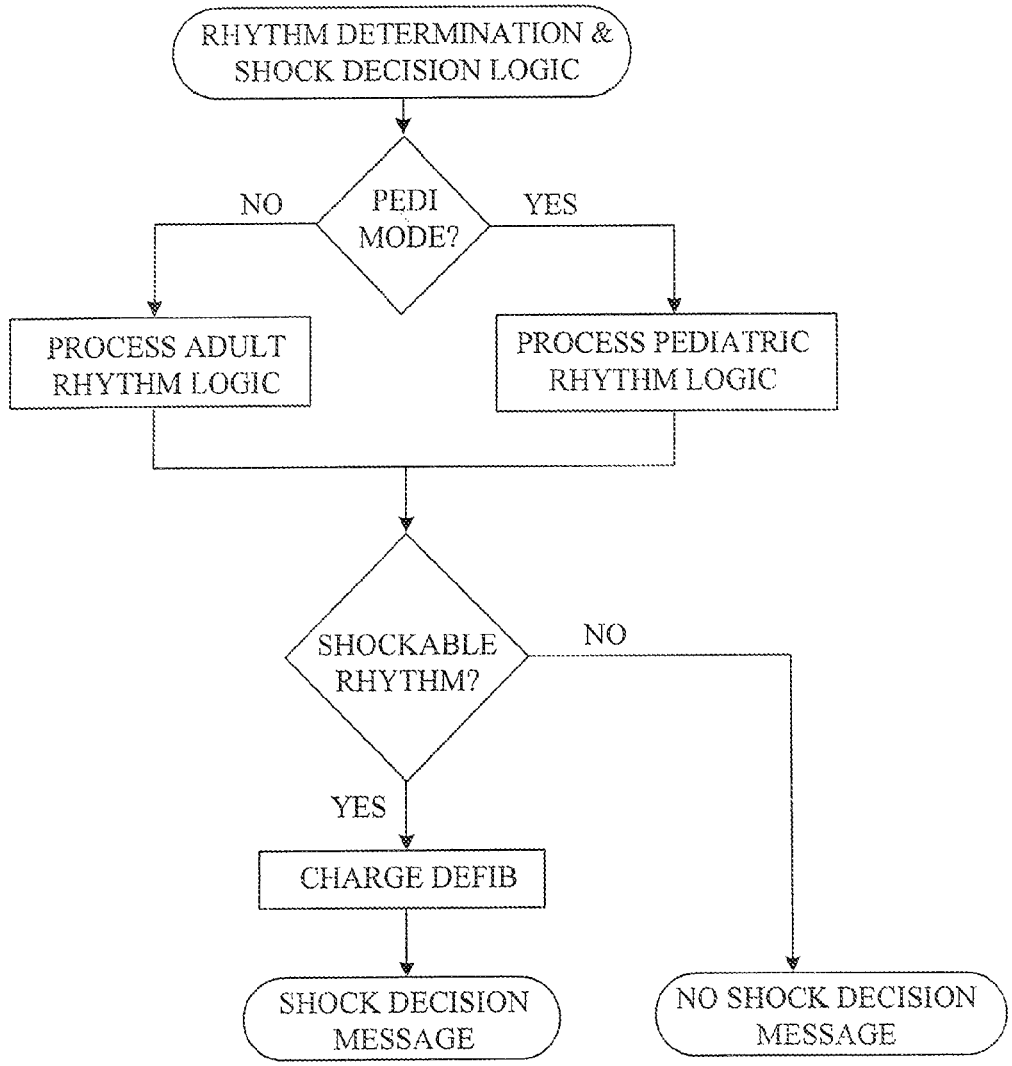
FIG. 14 is a flow diagram of mode specific processing for enhancing rhythm classification logic and shock determination.

FIG. 14 shows an example of the use of mode specific processing to enhance the rhythm classification logic and shock decision determination. The PEDI Mode Selection block chooses which Patient Mode Rhythm Logic to process. Rhythm classification logic can be implemented in a number of ways, heuristic (if-then-else) rules, feature cluster analysis, fuzzy system analysis, neural networks, Bayesian probabilistic system analysis, etc. The Shockable Rhythm Selection block selects the appropriate process flow based on the Shock decision. The No Shock Decision block notifies the defibrillator system to take the appropriate actions such as display and audibly announce the non-shockable rhythm analysis result. A shockable decision will produce a charging of the defibrillator and a delivery of therapy (automatic defibrillator) or a prompt to the user for delivery of energy (semi-automatic defibrillator).

FIG. 15 and FIG. 16 are simple examples adult and pediatric AED arrhythmia logic tables. The rhythm classifications in column 1 are satisfied when all of the rules stated in columns 2-6 are met and the respective shock decision is listed in the last column. The examples show that the shockable versus non-shockable decision can come from specific adult or pediatric rhythm classification logic. The various limits, rules, or other population specific logic systems are tuned (or trained) from adult and pediatric ECG signal databases, respectively.

Figure 7:
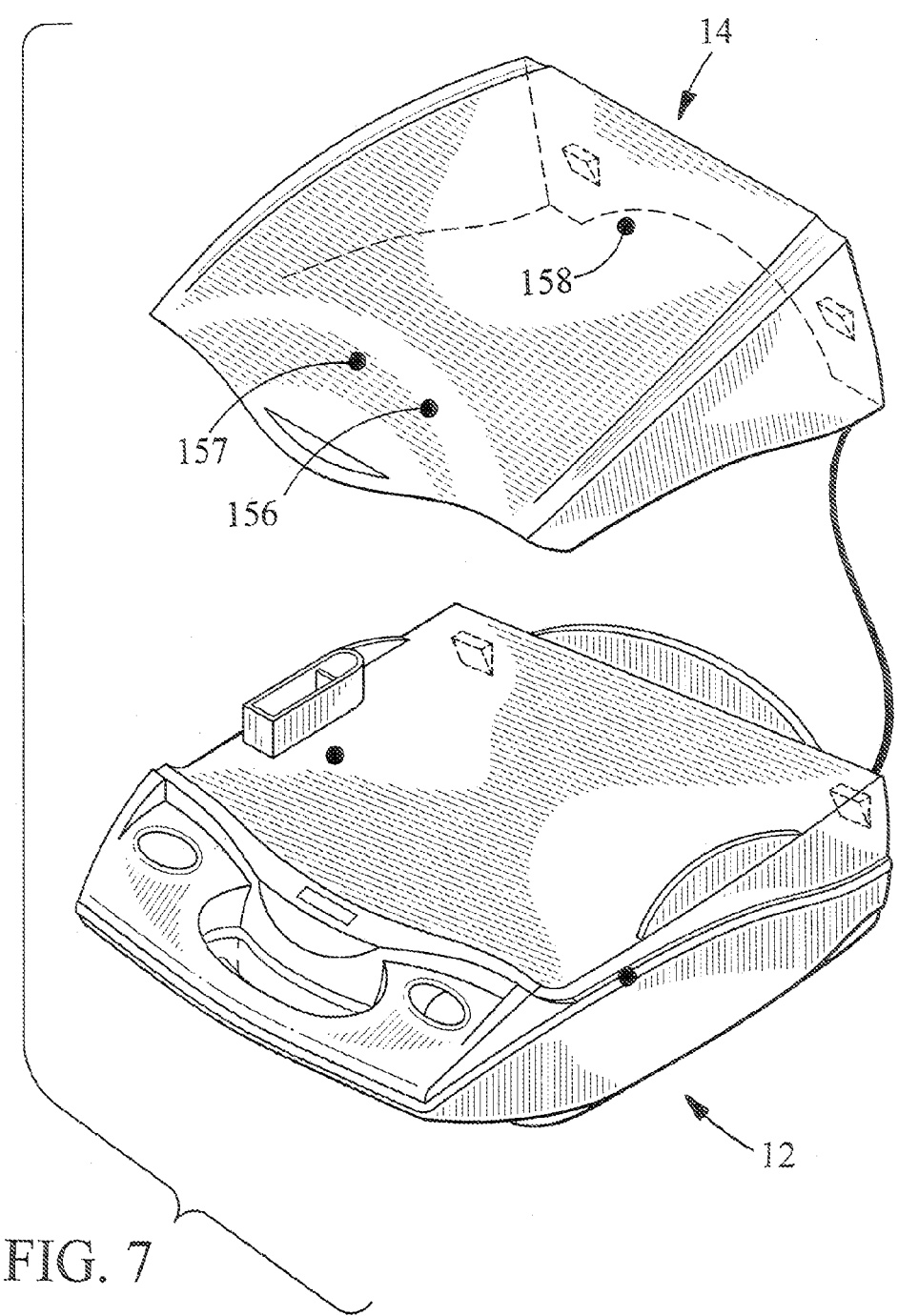
FIG. 7 shows an exploded perspective view of the cover and housing.
Figure 8:
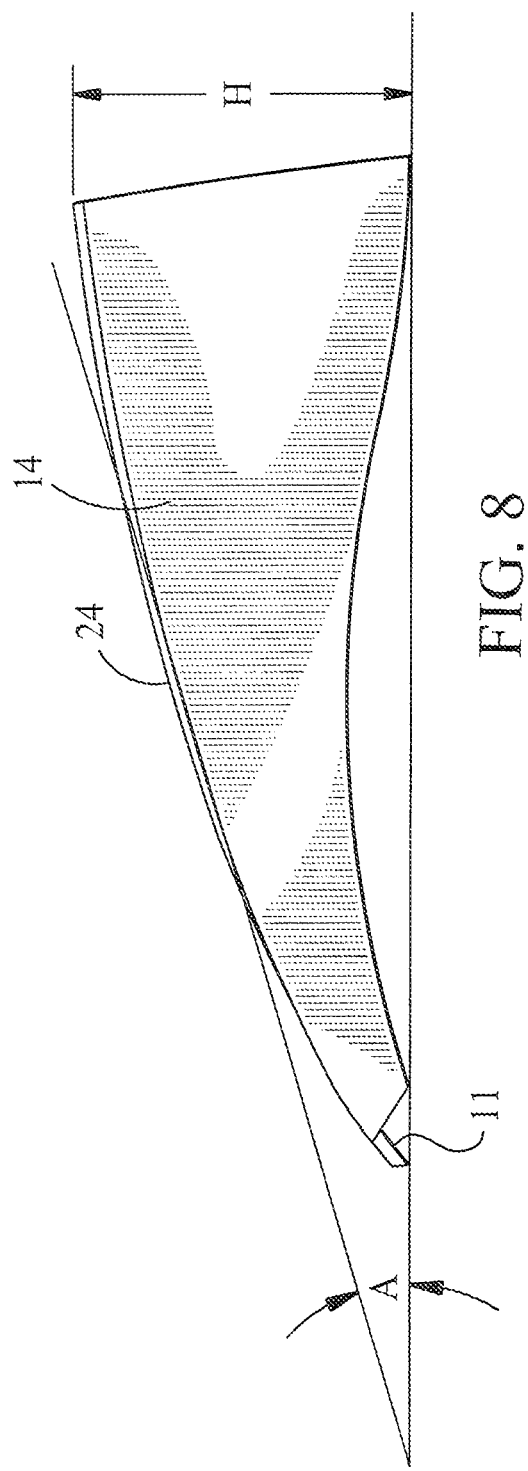
FIG. 8 shows a side plan view of the cover indicating angle 'A'.

Referring to FIG. 7, the cover 12 is provided with a detection means for determining if the patient's shoulders have been properly positioned on the cover 12. Two photo-electric sensors 156, 157 are used to determine if the cover has been placed underneath the patient's back. The sensors 156, 157 are located along the acute edge of the cover 12, with one facing inward and one facing outward with the cable 155 providing both power to the sensors 156, 157 as well as detection of the sensor output. If the cover 12 is upside down, the inner sensor 156 will measure a higher light level than the outer sensor 157; if the cover has been placed with the acute edge facing toward the top of the patient's head, then the outer sensor 157 will measure higher than the inner sensor 156 and will also exceed a pre-specified level. In the case of a properly positioned cover, both inner 156 and outer sensor 157 outputs will be below a pre-specified level. In another embodiment, the detections means is provided by a pressure sensor 158 located underneath the cover decal. The pressure sensor 158 can be used to measure the thoracic weight of the victim. Based on the measured weight, a table lookup can be generated, determining the victim's approximate age as well as the optimal defibrillation energies to provide.

Thus, when a person collapses and a caregiver suspects that the person is in cardiac arrest, the caregiver first gets the defibrillator and turns the power on 102. If the unit passes its internal self tests, and is ready for use, this will be indicated by indicator 17. Next, the defibrillator prompts the caregiver with an introductory audio message, e.g., "Stay calm. Listen carefully."

Shortly thereafter, the defibrillator will prompt the caregiver with an audio message indicating that the caregiver should check the patient for responsiveness. Simultaneously, the LED 56 adjacent graphic 42 will light up, directing the caregiver to look at this graphic. Graphic 42 will indicate to the caregiver that she should shout "are you OK?" and shake the person in order to determine whether the patient is unconscious or not.

After a suitable period of time has elapsed (e.g., 2 seconds), if the caregiver has not turned the defibrillator power off (as would occur if the patient were responsive), the defibrillator will give an audio prompt indicating that the caregiver should call for help. Simultaneously, the LED adjacent graphic 42 will turn off and the LED adjacent graphic 43 will light up, directing the caregiver's attention to graphic 43. Graphic 43 will remind the caregiver to call emergency personnel, if the caregiver has not already done so.

After a suitable interval has been allowed for the caregiver to perform the prior step (e.g., 2 seconds) the defibrillator will give an audio prompt indicating that the caregiver should open the patient's airway and check whether the patient is breathing. The LED adjacent graphic 43 will turn off, and the LED adjacent graphic 44 will light up, directing the caregiver's attention to graphic 44, which shows the proper procedure for opening a patient's airway. This will lead the caregiver to lift the patient's chin and tilt the patient's head back. The caregiver may also position an airway support device under the patient's neck and shoulders, if desired, as discussed below with reference to FIGS. 9a, 9b. The caregiver will then check to determine whether the patient is breathing.

After a suitable interval (e.g., 15 seconds), the defibrillator will give an audio prompt indicating that the caregiver should check for signs of circulation, the LED adjacent graphic 44 will turn off, and the LED adjacent graphic 45 will light up. Graphic 45 will indicate to the caregiver that the patient should be checked for a pulse or other signs of circulation as recommended by the AHA for lay rescuers.

After a suitable interval (e.g., 5 to 7 seconds), the defibrillator will give an audio prompt indicating that the caregiver should attach electrode assembly 16 to the patient, the LED adjacent graphic 45 will turn off, and the LED adjacent graphic 46 will light up. Graphic 46 will indicate to the caregiver how the electrode assembly 16 should be positioned on the patient's chest.

At this point, the LED adjacent graphic 47 will light up, and the defibrillator will give an audio prompt indicating that the patient's heart rhythm is being analyzed by the defibrillator and the caregiver should stand clear. While this LED is lit, the defibrillator will acquire ECG data from the electrode assembly, and analyze the data to determine whether the patient's heart rhythm is shockable. This analysis is conventionally performed by AEDs.

If the defibrillator determines that the patient's heart rhythm is not shockable, the defibrillator will give an audio prompt such as "No shock advised". The LEDs next to graphics 48 and 49 will then light up, and the defibrillator will give an audio prompt indicating that the caregiver should again open the patient's airway, check for breathing and a pulse, and, if no pulse is detected by the caregiver, then commence giving CPR. Graphics 48 and 49 will remind the caregiver of the appropriate steps to perform when giving CPR.

Alternatively, if the defibrillator determines that the patient's heart rhythm is shockable, the defibrillator will give an audio prompt such as "Shock advised. Stand clear of patient. Press treatment button." At the same time, the heart 54 and/or hand 52 will light up, indicating to the caregiver the location of the treatment button. At this point, the caregiver will stand clear (and warn others, if present, to stand clear) and will press the heart 54, depressing the treatment button and administering a defibrillating shock (or a series of shocks, as determined by the defibrillator electronics) to the patient.

Figure 11:
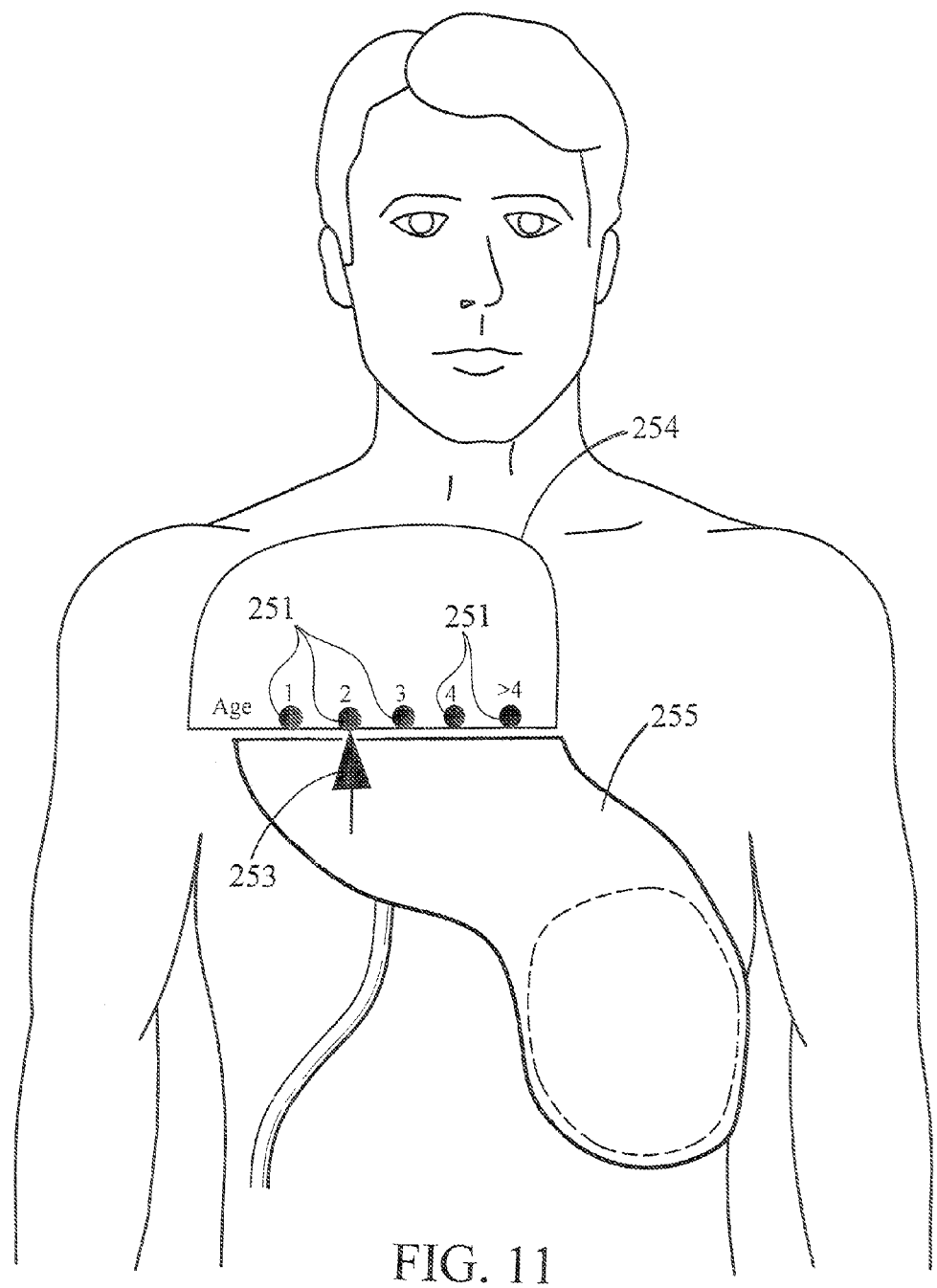
FIG. 11 shows an integrated electrode pad.

Referring to FIG. 11, in some implementations, a means is provided of detecting the relative lateral positions of the apex electrode 255 and the sternum electrode 254. In one implementation, magnetic Hall Effect sensors 251 are located such that when activated by the magnet 253 located within the apex electrode 255 the signal generated by the Hall effect sensor 251 indicates the relative lateral location of the electrodes. Using known anthropometrics, the thoracic girth can be estimated as well as patient age and defibrillation energy levels. The relative lateral positions of the electrodes can be determined using a linear encoder commonly used in digital calipers thus providing an accurate measurement of girth. The encoder may be an optical encoder or a magnetic based encoder.

Figure 10:
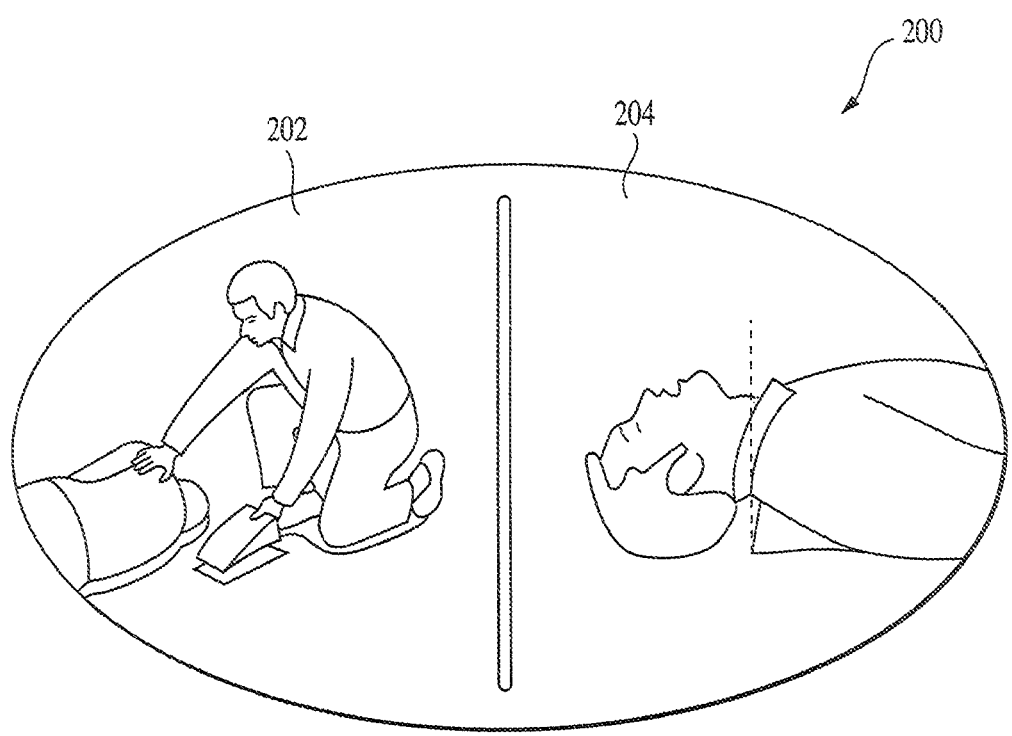
FIG. 10 shows the graphical instructions on the cover for placing the cover under a patient's shoulders.

The cover 12 of the AED may include a decal on its underside, e.g., decal 200 shown in FIG. 10. Decal 200 illustrates the use of the cover as a passive airway support device, to keep the patient's airway open during resuscitation. Graphic 202 prompts the caregiver to roll the patient over and place cover 12 under the patient's shoulders, and graphic 204 illustrates the proper positioning of the cover 12 under the patient to ensure an open airway.

Figure 5:
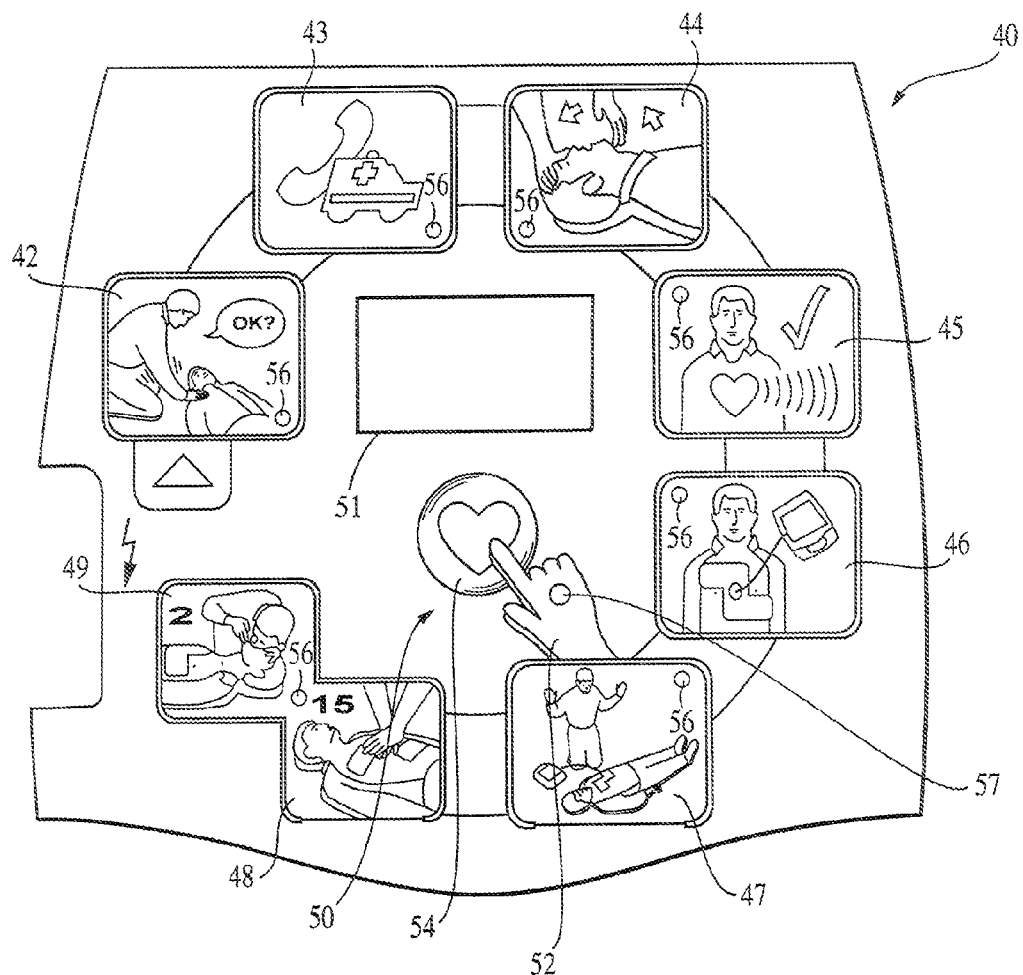
FIG. 5 is a plan view of the graphical interface decal used on the device housing of the AED of FIG. 1, as shown in FIG. 2.

While such a graphic is not included in the decal shown in FIG. 5, the decal 40 may include a graphic that would prompt the user to check to see if the patient is breathing. Such a graphic may include, e.g., a picture of the caregiver with his ear next to the patient's mouth. The graphic may also include lines indicating flow of air from the patient's mouth.

Many other implementations of the invention other than those described above are within the invention, which is defined by the following claims.

What is claimed is:

1. An external defibrillation device for assisting a rescuer in delivering defibrillation therapy to an adult or pediatric patient, the device comprising
a user interface comprising a display or audio speakers, the user interface being configured to deliver prompts to a rescuer to assist the rescuer in delivering therapy to a patient;
processing circuitry configured to provide prompts to the user interface and to perform an ECG analysis algorithm on ECG information detected from the patient;
defibrillation electrodes for placement on the chest of the patient;
one or more sensors located in and/or supported by one or both of the defibrillation electrodes, the sensors and processing circuitry being configured to use at least one output from one of the sensors to determine a distance between the electrodes after they are placed on the patient's chest;
wherein the processing circuitry is configured to determine information pertaining to the size of the patient from the distance determined from the output of one or more sensors, and wherein the processing circuitry is configured to vary the prompts, or the ECG analysis algorithm, or the energy delivered to the patient based on the information pertaining to the size of the patient.

2. The device of claim 1 wherein the processing circuitry is further configured to estimate the circumferential girth of the patient from the information obtained from the sensors.

3. The device of claim 1 wherein the processing circuitry is further configured to estimate an age or age range, such as pediatric and adult, of the patient from the information obtained from the sensors.

4. The device of claim 1 wherein there are at least two sensors, one located in and/or supported by each of two of the defibrillation electrodes, and the sensors and processing circuitry are configured to use the one output from one of the sensors and another output from the other sensor to determine the distance between the electrodes.

5. The device of claim 1 wherein the sensors and processing circuitry are configured so that the sensors automatically provide the at least one output to the processing circuitry after the electrodes are electrically connected to the processing circuitry, without user interaction with the device beyond making the electrical connection.

6. The device of claim 5 wherein the sensors function without mechanical movement of elements of the sensors.

7. The device of claim 6 wherein the sensors function without a mechanical connection between the two electrodes other than an electrical cable.

8. The device of claim 6 wherein the sensors comprise electromagnetic elements configured so that relative movement of the electrodes decreasing or increasing the distance between the electrodes produces a change in an electrical or magnetic field that is detectable by at least one of the sensors.

9. The device of claim 1 wherein at least one of the sensors detects change in the distance between the electrodes without mechanical movement of elements in the sensors.

10. The device of claim 1 wherein at least one of the sensors detects change in the distance between the electrodes by sensing a change in one or more of light, sound, electrical field, and magnetic field.

11. The device of claim 1 wherein the one or more sensors comprise Hall Effect sensors.

12. The device of claim 1 wherein there are one or more Hall Effect sensors and one or more magnets located in and/or supported by the electrodes so that relative motion between the two electrodes produces a change in the outputs of the Hall Effect sensors.

13. The device of claim 11 wherein there are two or more Hall Effect sensors located in and/or supported by one of the defibrillation electrodes and at least one magnet located in and/or supported by the other of the defibrillation electrodes.

14. The device of claim 1 wherein sensors comprise a linear encoder.

15. The device of claim 14 wherein the linear encoder is an optical encoder or a magnetic based encoder.

16. The device of claim 1 wherein the distance is any of the following: a relative lateral distance in the direction in which a girth measurement is taken, a physical separation between the electrodes, a straight line distance between a predetermined location on each of the electrodes.

17. The device of claim 1 wherein each defibrillation electrode comprises an assembly of at least the following: a skin-contacting conductive gel layer, an adhesive element surrounding the gel layer for adhering the electrode to the skin of the patient, a metallic current spreading element above the gel layer, and a non-conductive flexible base layer.

* * * * *